United States Patent
Quevy et al.

(10) Patent No.: US 9,422,149 B2
(45) Date of Patent: Aug. 23, 2016

(54) TRAPPED SACRIFICIAL STRUCTURES AND METHODS OF MANUFACTURING SAME USING THIN-FILM ENCAPSULATION

(71) Applicant: Semiconductor Manufacturing International (Shanghai) Corporation, Shanghai (CN)

(72) Inventors: Emmanuel P. Quevy, El Cerrito, CA (US); Louis Nervegna, Andover, MA (US); Jeremy R. Hui, San Jose, CA (US)

(73) Assignee: SEMICONDUCTOR MANUFACTURING INTERNATIONAL (SHANGHAI) CORPORATION, Shanghai (CN)

( * ) Notice: Subject to any disclaimer, the term of this patent is extended or adjusted under 35 U.S.C. 154(b) by 0 days.

(21) Appl. No.: 14/532,723

(22) Filed: Nov. 4, 2014

(65) Prior Publication Data
US 2016/0025664 A1    Jan. 28, 2016

Related U.S. Application Data

(60) Provisional application No. 62/029,233, filed on Jul. 25, 2014.

(51) Int. Cl.
*B81B 3/00* (2006.01)
*B81B 7/00* (2006.01)
(Continued)

(52) U.S. Cl.
CPC .............. *B81B 3/0021* (2013.01); *B81B 7/008* (2013.01); *B81B 7/0077* (2013.01); *B81C 1/0038* (2013.01); *B81C 1/00158* (2013.01); *B81C 1/00246* (2013.01); *B81C 1/00285* (2013.01); *B81C 1/00333* (2013.01); *G01N 27/223* (2013.01); *B81B 2201/0214* (2013.01); *B81B 2201/0235* (2013.01); *B81B 2201/0264* (2013.01); *B81B 2203/0127* (2013.01);
(Continued)

(58) Field of Classification Search
CPC .................... B81C 1/00246; B81C 1/00285
See application file for complete search history.

(56) References Cited

U.S. PATENT DOCUMENTS

| 4,838,088 A | 6/1989 | Murakami |
| 5,188,983 A | 2/1993 | Guckel et al. |

(Continued)

FOREIGN PATENT DOCUMENTS

| WO | WO2005/061376 A1 | 7/2005 |
| WO | WO2006/081636 A1 | 8/2006 |

OTHER PUBLICATIONS

Jahnes et al., "Simultaneous Fabrication of RF MEMS Switches and Resonators Using Copper-Based CMOS Interconnect Manufacturing Methods", IEEE, 2004, 4 pgs.

(Continued)

*Primary Examiner* — Mohammad Islam
*Assistant Examiner* — Ankush Singal
(74) *Attorney, Agent, or Firm* — Kilpatrick Townsend & Stockton LLP

(57) ABSTRACT

Trapped sacrificial structures and thin-film encapsulation methods that may be implemented to manufacture trapped sacrificial structures such as relative humidity sensor structures, and spacer structures that protect adjacent semiconductor structures extending above a semiconductor die substrate from being contacted by a molding tool or other semiconductor processing tool in an area of a die substrate adjacent the spacer structures.

11 Claims, 13 Drawing Sheets

(51) Int. Cl.
  *B81C 1/00* (2006.01)
  *G01N 27/22* (2006.01)
(52) U.S. Cl.
  CPC . *B81C2203/0136* (2013.01); *B81C 2203/0172* (2013.01); *B81C 2203/0735* (2013.01)

(56) References Cited

U.S. PATENT DOCUMENTS

| | | | |
|---|---|---|---|
| 5,470,797 A | 11/1995 | Mastrangelo | |
| 5,589,082 A | 12/1996 | Lin et al. | |
| 5,893,974 A | 4/1999 | Keller et al. | |
| 5,919,364 A | 7/1999 | Lebouitz et al. | |
| 5,919,548 A | 7/1999 | Barron et al. | |
| 6,160,705 A | 12/2000 | Stearns et al. | |
| 6,197,691 B1 | 3/2001 | Lee | |
| 6,210,988 B1 | 4/2001 | Howe et al. | |
| 6,335,224 B1 | 1/2002 | Peterson et al. | |
| 6,429,755 B2 | 8/2002 | Speidell et al. | |
| 6,499,354 B1 | 12/2002 | Najafi et al. | |
| 6,613,241 B1 | 9/2003 | Scherer et al. | |
| 6,635,509 B1 | 10/2003 | Ouellet | |
| 6,844,214 B1 | 1/2005 | Mei et al. | |
| 6,897,551 B2 | 5/2005 | Amiotti | |
| 6,902,656 B2 | 6/2005 | Quellet et al. | |
| 6,923,625 B2 | 8/2005 | Sparks | |
| 6,936,494 B2 | 8/2005 | Cheung | |
| 6,953,985 B2 | 10/2005 | Lin et al. | |
| 6,988,789 B2 | 1/2006 | Silverbrook | |
| 6,991,953 B1 | 1/2006 | Bruner et al. | |
| 7,002,436 B2 | 2/2006 | Ma et al. | |
| 7,008,812 B1 | 3/2006 | Carley | |
| 7,029,829 B2 | 4/2006 | Stark et al. | |
| 7,045,958 B2 | 5/2006 | Ramamoorthi et al. | |
| 7,061,099 B2 | 6/2006 | Lu et al. | |
| 7,074,636 B2 | 7/2006 | Curtis et al. | |
| 7,075,160 B2 * | 7/2006 | Partridge et al. | 257/414 |
| 7,078,268 B1 | 7/2006 | Geosling | |
| 7,115,436 B2 | 10/2006 | Lutz et al. | |
| 7,344,907 B2 | 3/2008 | Colgan et al. | |
| 7,595,209 B1 | 9/2009 | Monadgemi et al. | |
| 7,648,859 B2 | 1/2010 | Robert | |
| 7,659,150 B1 * | 2/2010 | Monadgemi et al. | 438/125 |
| 7,736,929 B1 | 6/2010 | Monadgemi et al. | |
| 7,923,790 B1 * | 4/2011 | Quevy et al. | 257/415 |
| 7,956,428 B2 | 6/2011 | Yama | |
| 8,007,167 B2 | 8/2011 | Cummins | |
| 8,273,594 B2 | 9/2012 | Quevy et al. | |
| 8,288,835 B2 | 10/2012 | Quevy et al. | |
| 8,313,970 B2 | 11/2012 | Quevy et al. | |
| 8,338,282 B2 | 12/2012 | Pornin et al. | |
| 8,786,130 B1 | 7/2014 | Mori et al. | |
| 2002/0151100 A1 | 10/2002 | Coffa et al. | |
| 2003/0148550 A1 | 8/2003 | Volant et al. | |
| 2003/0215974 A1 | 11/2003 | Kawasaki et al. | |
| 2004/0196608 A1 | 10/2004 | Anderson et al. | |
| 2004/0224091 A1 | 11/2004 | Rusu et al. | |
| 2005/0176179 A1 | 8/2005 | Ikushima et al. | |
| 2005/0179099 A1 | 8/2005 | Lutz et al. | |
| 2005/0250236 A1 | 11/2005 | Takeuchi et al. | |
| 2006/0017533 A1 | 1/2006 | Jahnes et al. | |
| 2006/0063462 A1 | 3/2006 | Ding et al. | |
| 2006/0108652 A1 * | 5/2006 | Partridge et al. | 257/414 |
| 2006/0108675 A1 | 5/2006 | Colgan et al. | |
| 2006/0148137 A1 | 7/2006 | Hartzell et al. | |
| 2006/0228869 A1 | 10/2006 | Haluzak et al. | |
| 2007/0013268 A1 | 1/2007 | Kubo et al. | |
| 2007/0190680 A1 | 8/2007 | Fukuda et al. | |
| 2007/0298238 A1 * | 12/2007 | Witvrouw et al. | 428/304.4 |
| 2008/0164542 A1 * | 7/2008 | Yang et al. | 257/415 |
| 2009/0134492 A1 * | 5/2009 | Morris et al. | 257/532 |
| 2009/0179287 A1 | 7/2009 | Inaba | |
| 2011/0163399 A1 * | 7/2011 | Witvrouw et al. | 257/419 |
| 2012/0098074 A1 | 4/2012 | Lin et al. | |
| 2012/0211805 A1 | 8/2012 | Winkler et al. | |
| 2012/0261830 A1 | 10/2012 | Chu et al. | |
| 2012/0313235 A1 | 12/2012 | Chu et al. | |
| 2013/0193527 A1 | 8/2013 | Chu et al. | |
| 2014/0264648 A1 | 9/2014 | Chu et al. | |
| 2016/0023888 A1 | 1/2016 | Quevy et al. | |
| 2016/0023889 A1 | 1/2016 | Quevy et al. | |

OTHER PUBLICATIONS

Lund et al., "A Low Temperature BI-CMOS Compatible Process for MEMS RF Resonators and Filters", Solid State Sensor, Actuator and Microsystems Workshop, 2002, 4 pgs.

* cited by examiner

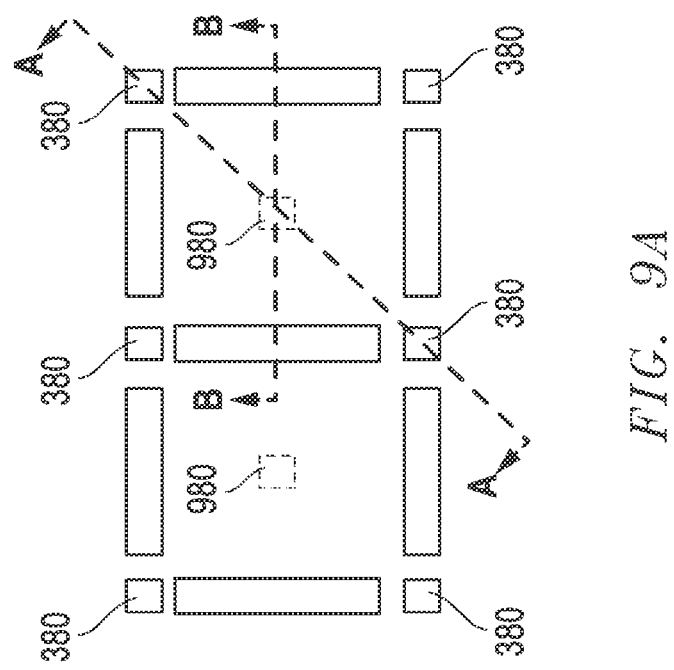
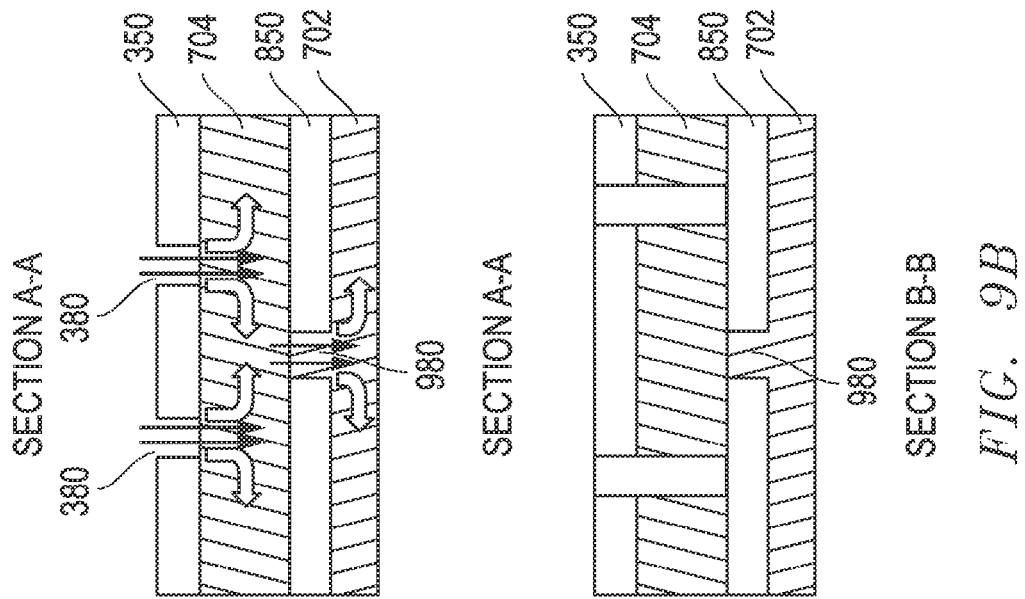
FIG. 9A
FIG. 9B

TRAPPED SACRIFICIAL STRUCTURES AND METHODS OF MANUFACTURING SAME USING THIN-FILM ENCAPSULATION

This application claims the benefit of U.S. Provisional Patent Application Ser. No. 62/029,233, filed on Jul. 25, 2014 and entitled "Methods And Structures For Thin-Film Encapsulation And Co-Integration Of Same With Microelectronic Devices And Microelectromechanical Systems (MEMS)", which is incorporated herein by reference in its entirety for all purposes.

The present application is related in subject matter to concurrently-filed patent application Ser. No. 14/532,675 entitled "Membrane Transducer Structures and Methods of Manufacturing Same Using Thin-Film Encapsulation" by Quevy et al., and to concurrently filed patent application Ser. No. 14/532,658 entitled "Methods and Structures for Thin-Film Encapsulation And Co-Integration of Same with Microelectronic Devices And Microelectromechanical Systems (MEMS)" by Quevy et al., each of which is filed on the same date as the present application and each of which is incorporated herein by reference in its entirety.

FIELD OF THE INVENTION

This invention relates generally to semiconductor processing, and more particularly to thin-film encapsulation and co-integration of same with microelectronic devices and microelectromechanical systems (MEMS).

BACKGROUND

The term "MEMS" generally refers to an apparatus incorporating some mechanical structure having a dimensional scale that is comparable to microelectronic devices. Micro-scale fabrication techniques similar to those utilized in the microelectronic industry such as thin film deposition, and thin film patterning by photolithography and reactive ion etching (RIE) form the micromechanical structure in a MEMS.

In the past, multi-layered, planar microshells have been used for encapsulation of devices such as MEMS and microelectronics.

SUMMARY

Disclosed herein are trapped sacrificial structures and thin-film encapsulation methods that may be implemented to manufacture trapped sacrificial structures such as relative humidity sensor structures, and spacer structures that may be provided on a semiconductor die to prevent a molding tool or other semiconductor processing tool from contacting the tops of other semiconductor structures disposed on the die substrate in an area adjacent the spacer structures. In one exemplary embodiment, trapped sacrificial structures may be manufactured by co-integrating processes for thin-film encapsulation and formation of microelectronic devices and microelectromechanical systems (MEMS). In another exemplary embodiment, structures having varying characteristics may be fabricated in one embodiment using the same basic process flow by selecting among different process options or modules for use with the basic process flow in order to create the desired structure/s. Embodiments of the disclosed methods and structures include, among other things, various process flow sequences as well as a variety of device design structures that may be advantageously enabled by the various process flow sequences.

The disclosed methods and structures may be implemented in one embodiment using a process flow that allows thin-film microshell structures to be defined in a manner that addresses challenges typically encountered with implementation of conventional thin microshell structures. In this regard, a process flow may be employed in one exemplary embodiment to form a vacuum cavity under a thin-film microshell structure that has a smaller volume than a conventional wafer-bonded cavity, while at the same time maintaining a level of vacuum within the smaller volume microshell cavity that is equivalent or comparable to the level of vacuum that is typically maintained within a larger volume of a conventional wafer-bonded cavity structure. Such a process flow may also be implemented in one exemplary embodiment to maintain thin-film microshell vacuum cavity yield and robustness against post-encapsulation flows, included wafer processing and packaging flows which for example may exhibit high levels of pressure (e.g., greater than about 10 MPa) during the package molding process. Other advantages over conventional microshell processing that may be realized by one or more embodiments of the disclosed methods and structures include compatibility of integration with higher thermal budget associated with additional post-processing steps, as well as a level of device and product reliability (e.g., including long term stability) when exposed to environmental stresses that is comparable to the device and product reliability that is possible with conventional wafer-bonded cavity structures.

In another embodiment, the disclosed methods and structures may be implemented using a process flow to define thin-film microshell structures in a manner that enables the co-integration and co-location of sensors, actuators and other types of MEMS devices, while at the same time leveraging some of the same process features and structural elements for both microshell and different device structures. In one exemplary embodiment, optional processing modules may be used to strengthen a microshell structure and decouple the function of specific steps. Even when implementation of these optional processing modules results in an increase in the number of process steps and/or patterning masks, it also eases the integration and process requirements (e.g., sidewall profile, CD, wafer uniformity, etc.).

For example, a patterning step on a single layer may be used to provide two functions and have two different specification requirements. Since these specifications might be challenging to achieve with a single patterning step, the two functions may be separated out into different steps that may be independently tuned for the specific purpose, e.g., in some ways similar to a dual damascene process, where the same copper layer is used for both routing and via connections. However, for a microshell structure, it may be possible to achieve both functions with only a single mask/patterning step.

Examples of possible exemplary and optional processing modules include, but are not limited to: formation of a lower (or inner) microshell beneath an upper (or outer) microshell to provide a second layer of support; forming a patterned version of an inner microshell to provide both support and inner release holes for underlying structural devices that are offset from outer release holes formed in an overlying outer microshell (e.g., offset inner release holes may be employed to reduce the restrictions on the outer shell release holes, thus increasing the number of release holes and reducing the release etch time); completely enclosing a microshell structure getter layer (e.g., such as titanium) in oxide to protect it from attack from a release etchant such as hydrogen peroxide ($H_2O_2$); use of a hardmask (e.g., $SiO_2$) for sacrificial patterning that may be used as a mold for creating a waffle-like support lattice to reinforce a microshell structure (e.g., such a hardmask may be added as an independent layer or may leverage the getter multi-layer stack mentioned above).

In one exemplary embodiment, a process flow may be provided that also has the capability of adding different process options so as to enable additional functionalities and capabilities, e.g., including pressure sensors, ultrasonic transducers, relative humidity (RH) sensors, infrared (IR) sensors, optical modulators, etc. Such processing options may be seamlessly inserted (or removed) without significantly impacting the remaining steps. Examples of such process options include, but are not limited to: use of a vertical sacrificial layer for ultrasonic transducers (e.g., a thin sacrificial layer may be placed over an existing structural layer, such as SiGe, to create a small vertical gap to a microshell structure); patterning of a sealing material (e.g., such as a sealing metal) on a microshell structure for pressure sensors, IR bolometers (e.g., the metal layer used to seal the microshell may be patterned to allow for IR transmission and/or to control mechanical properties of the membrane); polyimide or other sacrificial layer patterning for relative humidity sensors (e.g., polyimide may be deposited and patterned to create a relative humidity sensor, or alternatively an existing polyimide sacrificial layer may be preserved and not removed in the sacrificial etch, so that it may be exposed at this step).

In one respect, disclosed herein is method of forming a trapped sacrificial structure, comprising: providing a MEMS region over a substrate, the MEMS region including a MEMS structural layer; forming a first sacrificial layer over the MEMS structural layer; removing a part of the first sacrificial layer to leave at least a remaining portion of the first sacrificial layer disposed over the MEMS structural layer; forming a second sacrificial layer over the remaining portion of the first sacrificial layer; removing a part of the second sacrificial layer to leave a portion of the second sacrificial layer; forming an upper micro shell layer over the remaining portions of the first and second sacrificial layers; creating one or more upper release holes in the upper microshell layer; and removing at least a part of the remaining portions of the first and/or second sacrificial layers through the upper release holes without removing a first sacrificial layer portion and/or a second sacrificial layer portion under the upper microshell layer to form at least one trapped sacrificial structure under the upper microshell layer.

In another respect, disclosed herein is a trapped sacrificial structure, comprising: a MEMS region disposed over a substrate, the MEMS region including a MEMS structural layer; a portion of a first sacrificial layer and a portion of a second sacrificial layer disposed over the MEMS structural layer; an upper microshell layer disposed over the portions of the first and second sacrificial layers, the first sacrificial layer portion and/or a second sacrificial layer portion being configured to form at least one trapped sacrificial structure under the upper microshell layer; and one or more upper release holes defined in the upper microshell layer.

BRIEF DESCRIPTION OF THE DRAWINGS

FIG. 9A illustrates an overhead view showing a pattern of offset microshell release holes according to one exemplary embodiment of the disclosed methods and structures.

FIG. 9B illustrates cross-sectional views of offset microshell release holes according to one exemplary embodiment of the disclosed methods and structures.

DESCRIPTION OF ILLUSTRATIVE EMBODIMENTS

Figure 1:
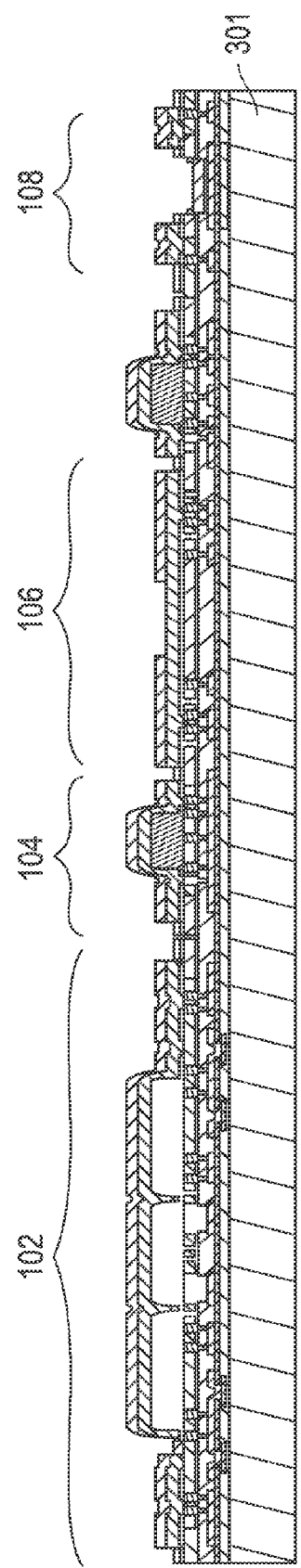
FIG. 1 illustrates a simplified cross-sectional view of different exemplary structures and devices that may be fabricated according to various embodiments of the disclosed systems and methods

FIG. 1 illustrates a simplified cross-sectional view of some of the different exemplary structures and devices that may be fabricated, alone or together, on a common die substrate 301 by selecting and using various processing options of the same basic process flow according to the disclosed systems and methods. In particular, FIG. 1 illustrates a vacuum encapsulated device structure 102 that includes a single structural layer microshell, a trapped sacrificial structure 104 (e.g., for a relative humidity sensor), a membrane transducer structure 106, and a shadow mask pad structure 108. As will be described further herein, one or more of these and/or other exemplary structures may be simultaneously fabricated (e.g., on a common substrate 301) using common processing features of a process flow and/or common structural elements. In this embodiment, whether or not optional layers are used, a process flow may be provided that allows co-location of different types of device structures as illustrated in FIG. 1. FIGS. 2A-2D illustrate the modular aspect of the disclosed process flows and the tradeoff between complexity and flexibility that may be made by choosing between the different process flows. It will be understood that in one embodiment, vacuum encapsulation is not necessary for any one or more of the above structures.

Figure 2A:
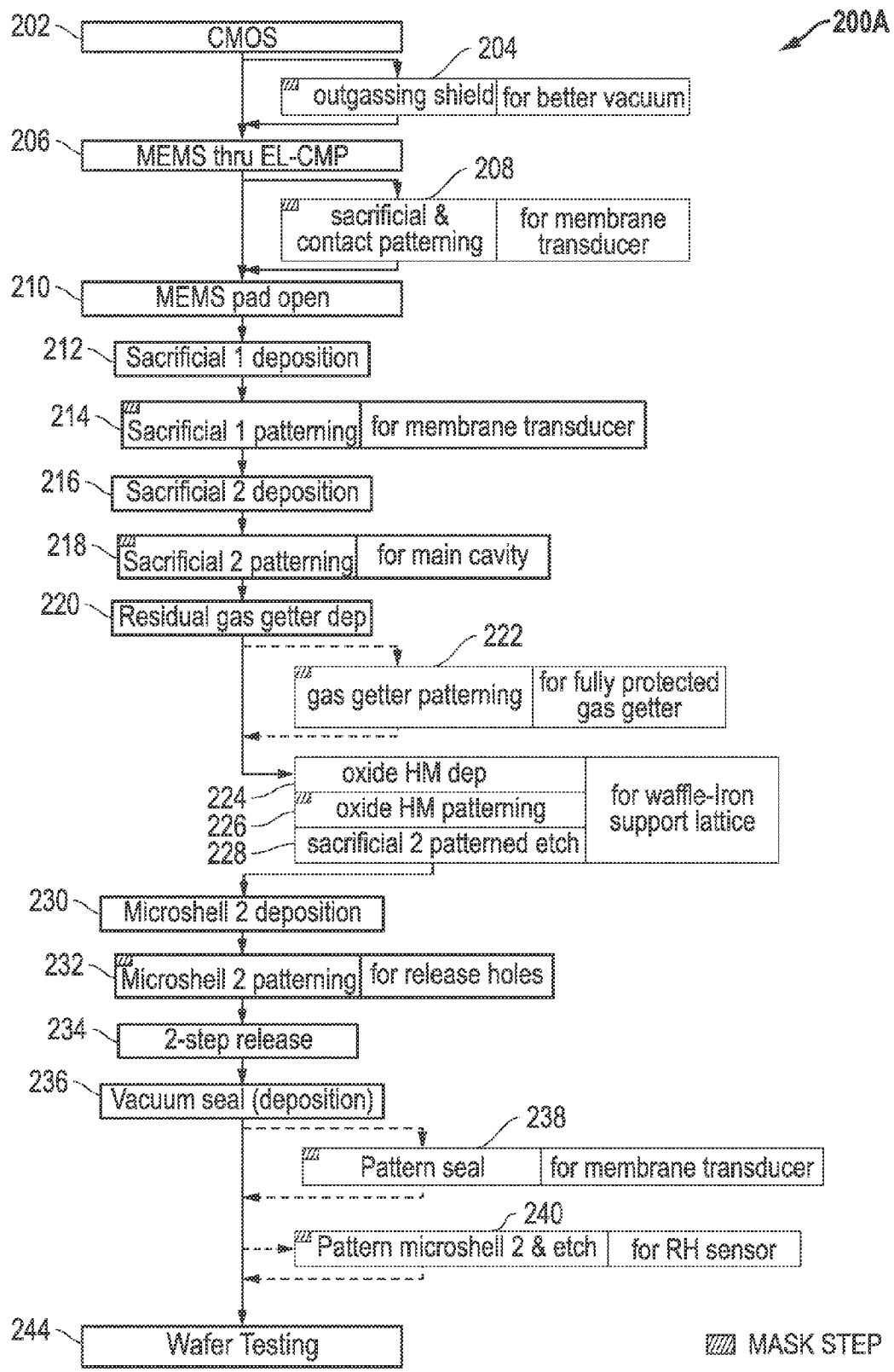
FIG. 2A illustrates a fabrication process flow according to one exemplary embodiment of the disclosed methods and structures.
Figure 2B:
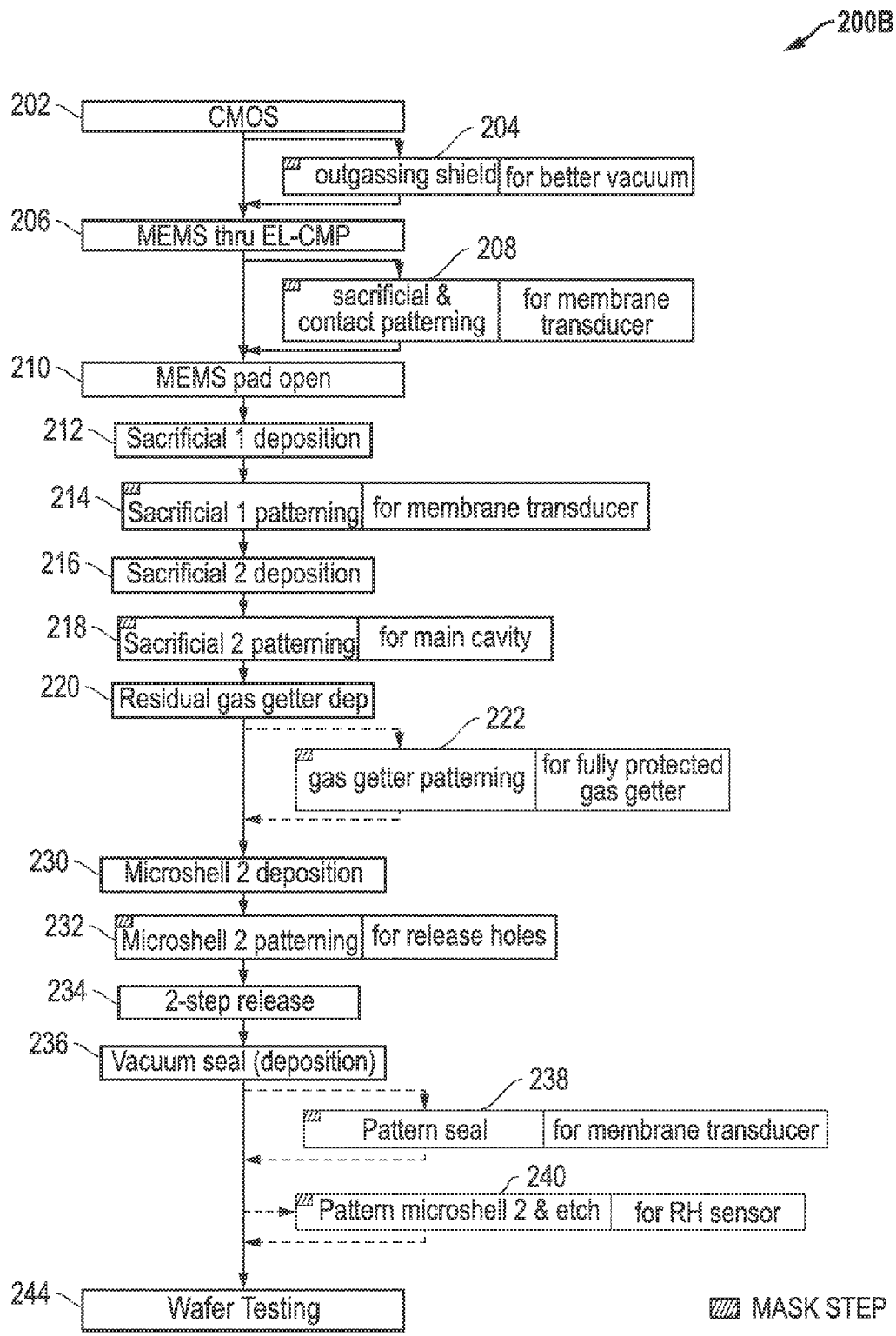
FIG. 2B illustrates a fabrication process flow according to one exemplary embodiment of the disclosed methods and structures.
Figure 2C:
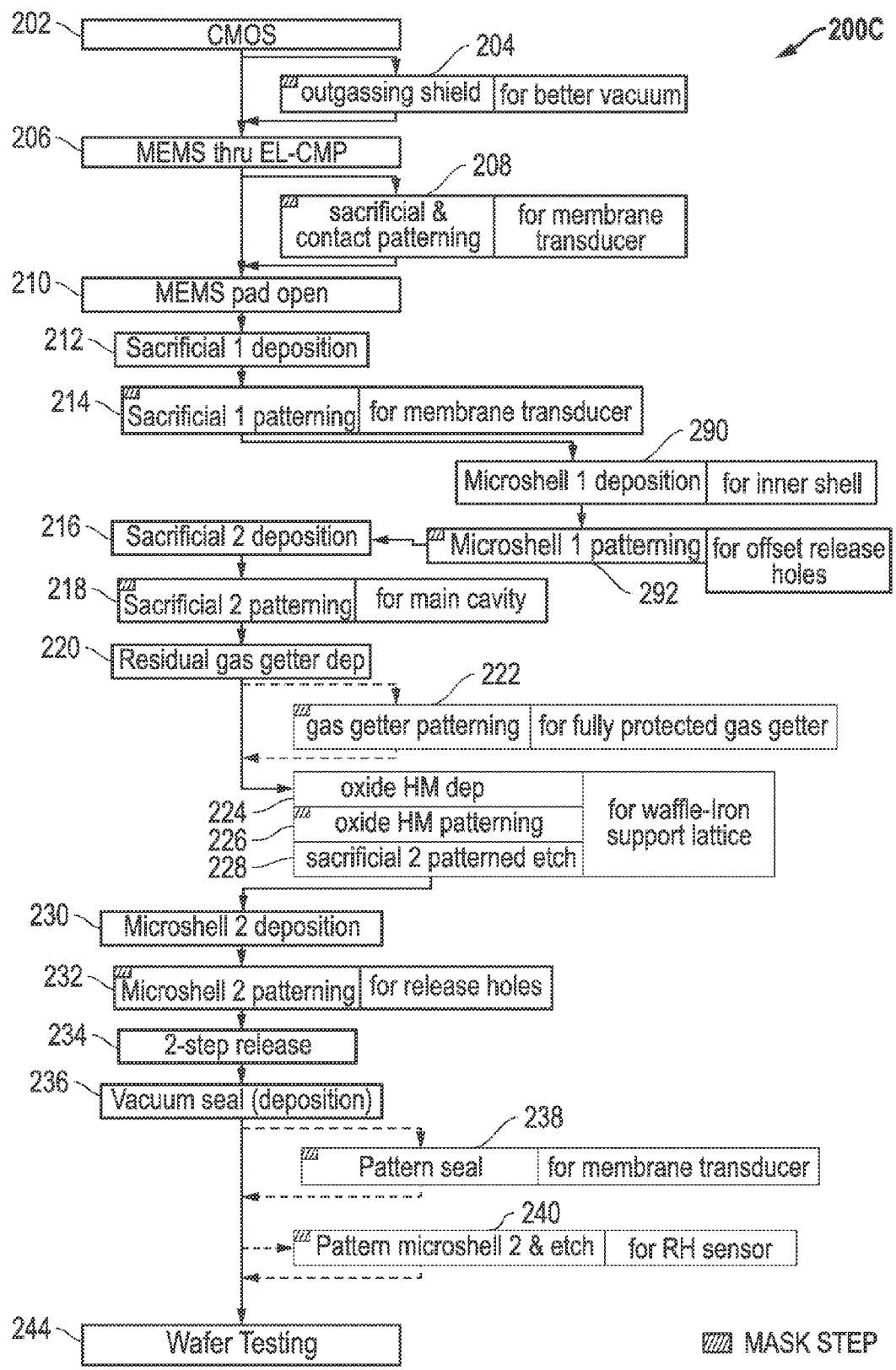
FIG. 2C illustrates a fabrication process flow according to one exemplary embodiment of the disclosed methods and structures.

It will be understood that the particular illustrated process flows of FIGS. 2A-2D are exemplary only, and that other combinations of fewer, additional, and/or alternative process steps may be employed. It will further be understood that each of the process flows of FIGS. 2A-2D may be varied to accommodate a number of materials for each process step. Relative complexity of the process flow embodiments of FIGS. 2A-2D may be ordered as follows (from most complex and most design flexibility to least complex and least design flexibility): FIG. 2C (most complex and most design flexibility)>FIG. 2D>FIG. 2A>FIG. 2B (least complex and least design flexibility).

With regard to the following description of process flows of FIGS. 2A-2D, Table 1 lists some of the exemplary materials and alternative materials that may be employed for some of the different layers described below to achieve the structures disclosed herein.

TABLE 1

| Layer | Exemplary Material Selection | Examples of Other Exemplary Alternatives |
| --- | --- | --- |
| Sacrificial 1 layer for CMUT vertical gap (321) | Ge | Amorphous Carbon (a-C) |
| Sacrificial 1 layer (702) | Polyimide | Ge, oxide, a-C |
| Microshell 1 layer (850) | SiGe | Oxide, nitride, TiAl, Ge, multi-layer (metal stack) |
| Sacrificial 2 layer (704) | Polyimide | Ge, oxide, a-C |
| Getter layer (334) | Ti | V, Zr, Ba |
| Microshell 2 layer (350) | SiGe | nitride, TiAl, W |
| Vacuum seal layer (390) | Al | PVD materials (SiGe, other metals) |

Figure 3:
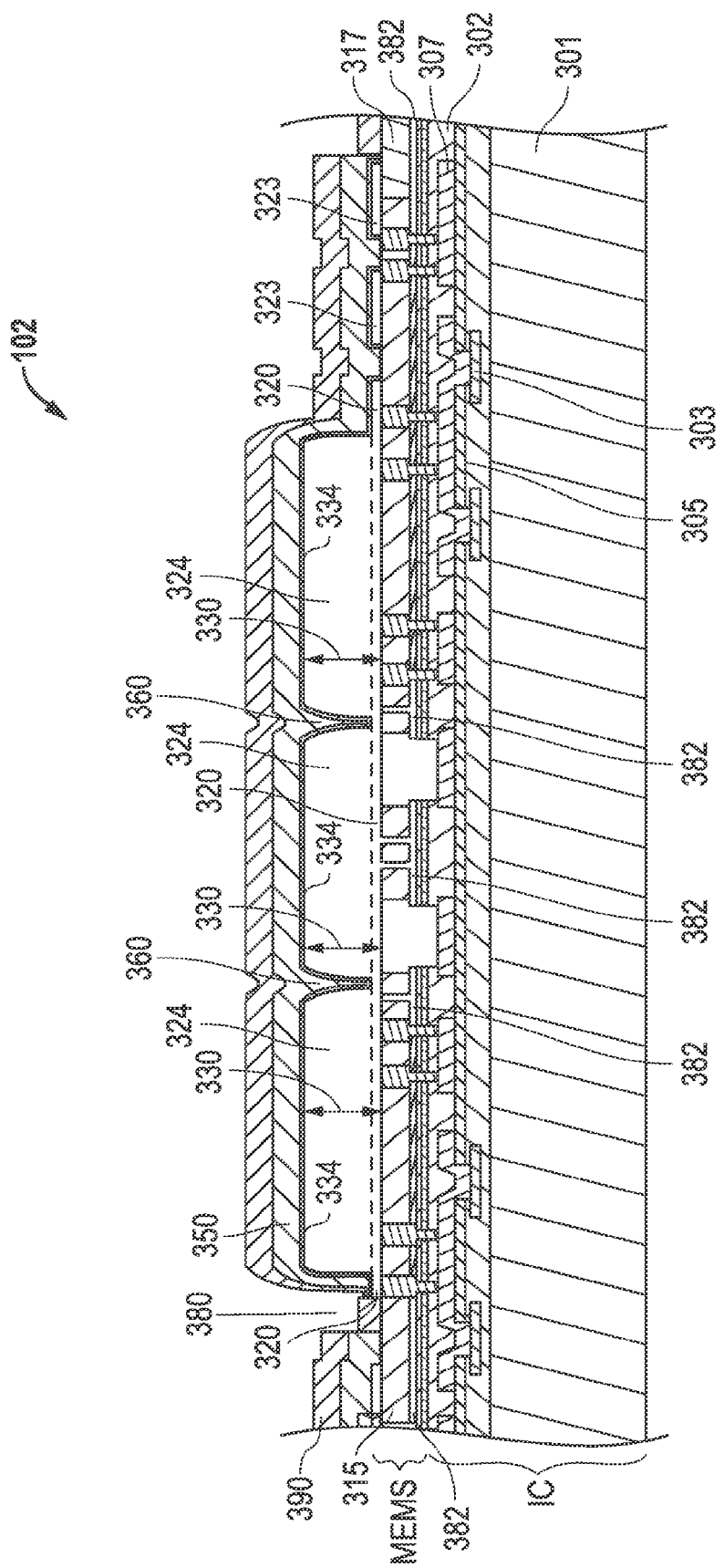
FIG. 3 illustrates a cross-sectional view of a vacuum encapsulated device structure according to one exemplary embodiment of the disclosed methods and structures.

FIG. 2A illustrates one exemplary embodiment of process flow 200A for forming a single structural layer microshell with a relatively thin but rigid underlying cavity such as illustrated by the vacuum encapsulated device structure 102 of FIG. 1. In the embodiment of FIG. 2A, steps 202 through 210 may be employed to form underlying integrated circuit ("IC") and MEMS regions of the structure of FIG. 1, e.g., using methodology such as described and illustrated in U.S. Pat. No. 7,923,790, which is incorporated herein by reference in its entirety for all purposes. In this regard, MEMS and IC portions may be completed using commonly known techniques, such as, but not limited to chemical vapor deposition (CVD), physical vapor deposition (PVD), electroplating, chemical mechanical planarization (CMP), patterned and unpatterned etching by wet chemicals or by reactive ion etching (RIE) plasmas. For example, FIG. 3 illustrates IC and MEMS regions formed according to one exemplary embodiment of steps 202-210. However, it will be understood that the disclosed methods and structures may be implemented for a variety of MEMS and microelectronics devices, and thus the formation of the MEMS and IC regions may vary substantially and therefore may deviate significantly from that depicted in FIG. 3.

In the exemplary embodiment of FIG. 3, formation of the IC portion or regions may include the deposition of interlayer dielectric (ILD) 302 over substrate 301 by CVD and deposition of metallizations 303 and 307, e.g., by PVD or electroplating over substrate 301. Metallizations 303 and 307 may be patterned lithographically and subsequently etched or metallizations 303 and 307 may deposited in pre-formed trenches in ILD 302 and subsequently delineated with chemical mechanical polishing (CMP) as in a common damascene metal interconnect process. Insulative layer or dielectric passivation layer 305 may be formed between metallizations 303 and 307, e.g., by chemical vapor deposition (CVD) followed by chemical mechanical polishing (CMP) to planarize. These illustrated layers represent the structures that may be found in one exemplary embodiment in a microelectronics IC region, it being understood that other IC region embodiments are possible. In one embodiment, the IC region may rely on any commonly known microelectronic transistor technology, such as, but not limited to MOSFET and bipolar junction transistors (BJT). In the practice of the disclosed system and methods it will be understood that devices and other structures (e.g., such as various MEMS devices and structures 102, 104, 106 and 108) may be integrated with an IC region as shown, or in an alternate embodiment may be present as discrete MEMS devices and other structures over a substrate 301.

Substrate 301 may be any commonly known semiconductor substrate, such as, but not limited to, single crystalline silicon, germanium or a silicon/germanium layer doped with an appropriate charge carrier. Substrate 301 may alternatively be comprised of a III-V material such as but not limited to gallium nitride, gallium phosphide, gallium arsenide, indium phosphide or indium antimonide. Moreover, substrate 301 may comprise an insulating layer such as silicon dioxide or silicon nitride embedded below a monocrystalline semiconductor layer to form, for example, a silicon on insulator or germanium on insulator substrate. Bulk insulators, such as sapphire, quartz, and glass may also be used.

Still referring to the exemplary embodiment of FIG. 3, a MEMS structural layer 315 may then be formed in one exemplary embodiment over the IC portion, e.g., using a damascene process. In general terms, a release layer (not shown) may be deposited, planarized, and etched with a desired pattern, e.g., to form blades or posts or other suitable or desired features. In a particular embodiment, such a release layer may be germanium deposited at a temperature of approximately 350° C. using a low pressure (LP) CVD process. Following the formation of the release layer, a MEMS structural layer 315 may then be deposited over the release layer and planarized to expose the blades, posts or other features of the release layer and thereby separate the structural layer into different segments. In a further embodiment, a dielectric material 317 such as polyimide or other suitable dielectric material such as described herein may be optionally deposited, patterned and etched prior to deposition of MEMS structural layer 315, e.g., to form selected areas of dielectric material 317 within MEMS structural layer 315 as illustrated herein. When present, such an optional dielectric material 317 may be selected to have selective sacrificial and etchant material properties relative to other layers as may be needed for a given application, such as for use in the area of release holes 380 and inlets 715 described further herein. In a particular embodiment employing a germanium release layer, MEMS structural layer 315 may be an alloy of silicon and germanium deposited at a temperature of approximately 425° C. using an LPCVD process. After fabricating the IC and MEMS regions, the thin-film encapsulation fabrication processes described further herein may be used to form microshell and/or device structures which may be incorporated at virtually any back end of line (BEOL) level of the typical IC fabrication process.

Returning to FIG. 2A, in step 212 a relatively thin first sacrificial layer may be deposited over MEMS structural layer 315 and then patterned and etched in step 214 to remove all but selected portions of the deposited first sacrificial layer to create a mold that will ultimately result in first cavity portion 320 (e.g., including peripheral open areas 320) and other open areas 323 when the first sacrificial layer is later removed as shown in FIG. 3. The first sacrificial layer may also be patterned and etched in step 212 to form other features in selected areas of the first sacrificial layer to be used for forming desired devices, e.g., such as a membrane transducer described later herein. In one exemplary embodiment, thickness of first sacrificial layer may be from about 0.5 µm to about 1 µm, although first sacrificial layer thicknesses of less than 0.5 µm and greater than 1 µm are also possible.

Next, in step 216, a relatively thicker second sacrificial layer may be deposited on top of the first sacrificial layer, and then patterned and etched in step 218, e.g., to create the mold for second thicker cavity portions 324. In one exemplary embodiment, thickness of the second sacrificial layer may be from about 5 µm to about 20 µm and alternatively from about 5 µm to about 15 µm, although first sacrificial layer thicknesses of less than 5 µm and greater than 20 µm are also possible. As will be further described, both first and second sacrificial layers may be subsequently removed to result in main cavity sections 330 of the exemplary embodiment of FIG. 3. In this regard, the dashed line extending across main cavity sections 330 in FIG. 3 serves to delineate the interface between the first and second sacrificial layers after second sacrificial layer deposition in step 218 prior to removal of the first and second sacrificial layers and deposition of an upper microshell layer 350 as described further herein. In one exemplary embodiment, multiple sacrificial layers may be deposited and removed to form a larger main cavity section 330 that maximizes cavity volume so as to better maintain vacuum and allow more room for the completed microshell structure to flex.

In one exemplary embodiment, the first cavity portions 320 and second cavity portions 324 may be formed to result in a multi-level cavity that enables different functionality of the upper microshell layer 350 to be created at different locations across the substrate 301, e.g., the thinner, first cavity portions 320 under microshell layer 350 may be used in one embodiment as a CMUT gap 321 for a membrane transducer 106 such as pressure sensor or other type transducer, and the main cavity sections 330 (i.e., including combined areas of first and second cavity portions 320 and 324) may be used for vacuum encapsulation for a vacuum encapsulated device structure 102, such as a MEMS resonator formed in MEMS structural layer 315.

To achieve the structure illustrated in FIG. 3, the first and second sacrificial layers may be of any suitable materials. For example, in one exemplary embodiment the first sacrificial layer may be deposited in step 212 as any one or more of polyimide, oxide, germanium, amorphous carbon, or other suitable sacrificial material, and then selectively etched after masking in step 214 using lithography and/or reactive ion etching (REI) to leave selected portions of the first sacrificial layer in areas corresponding to later-formed open areas 320 and 323 as previously described. The second sacrificial layer may then be deposited in this exemplary embodiment in step 216 as any one or more of polyimide, oxide, germanium, amorphous carbon, or other suitable sacrificial material, and then selectively etched after masking in step 218 using lithography and/or REI to leave portions of the second sacrificial material corresponding to the main cavity sections 330 on top of the previously patterned first sacrificial layer portions of areas 320, as well as to leave first sacrificial layer portions of areas 323, which each are selectively not removed in step 218. It is noted that selection of sacrificial material for each of first and second sacrificial layers may be made, among other things, based on at least two factors: dimensioning limits (e.g., thickness, critical dimension "CD", etc.) and material compatibility with other processes (e.g., processing temperature, glass transition temperature, decomposition temperature, etc.)

Next, in step 220, an optional residual gas getter layer 334 may be deposited (e.g., to a thickness of from about 0.1 µm to about 1 µm (alternatively about 0.3 µm) or any other suitable greater or lesser thickness) on top of the patterned first and second sacrificial layers in order to scavenge or otherwise remove contaminants from open areas 320, 323 and main cavity sections 330, including contaminants left behind from the etch of the first and/or second sacrificial layers after their removal, contaminants emitted by materials of the microshell layer 350, etc. In this regard, getter layer 334 may be configured to capture molecules, such as hydrogen, nitrogen, oxygen, water vapor, oxides of carbon, methane, etc. from within sections of areas 320, 323 and 330 after removal of first and second sacrificial layers. Examples of suitable materials for use as getter layer 334 include, but are not limited to, titanium, aluminum, vanadium, zirconium, barium-based compounds, etc. An optional oxide-based protective layer may be formed on the cavity-side surface of the getter layer 334 to prevent sacrificial etchants from prematurely damaging the getter layer 334 during patterning. In one embodiment, such protective layer may be an oxide of silicon of silicon, such as silicon dioxide ($SiO_2$), or other material that provides good selectivity to etchants of the first and second sacrificial layers. For example, a protective oxide layer has good selectivity to oxygen plasma that may be employed for etching polyimide or amorphous carbon sacrificial layers, polyimide has good selectivity to vapor HF or liquid HF etchants that may be employed for etching silicon dioxide sacrificial layers, and many protective materials have good selectivity to peroxide that may be employed for etching germanium sacrificial layers, etc. Further information on getter layer configuration and materials for protecting getter layers may be found in U.S. Pat. No. 7,923, 790, which is incorporated herein by reference in its entirety.

In step 222, deposited getter layer 334 may be optionally masked and patterned by reactive ion etching (RIE), ion milling, lift off, or any of a variety of other etching or patterning techniques for purposes of limiting the extent of getter layer 334 to areas of first cavity 320 and second cavity 324, and/or to prevent electrical coupling of getter layer 334 with underlying devices formed on or in MEMS region/structural layer 315 (e.g., such as inductors).

After optional deposition and patterning of gas getter layer 334, an oxide hard mask layer (e.g., $SiO_2$ or other suitable hard mask material) may be deposited in step 224 (e.g., by plasma enhanced chemical vapor deposition) and then patterned (e.g., by photolithography and resist) in step 226 to create a hard mask used to etch a mold into the second sacrificial layer in step 228 for forming microshell support lattice members 360 upon later deposition of upper microshell layer 350 as further illustrated and described with regard to FIG. 4.

Next, an upper microshell layer is deposited in step 230 over the first and second sacrificial layers and the getter layer 334 to create an upper microshell layer structure 350 as illustrated in FIG. 3. The upper microshell layer may in one embodiment be a silicon germanium (SiGe) material layer that is deposited by a low-pressure chemical vapor deposition (LPCVD) or plasma-enhanced chemical vapor deposition (PECVD) process to a thickness of from about 1 µm to about 2 µm at locations other than at support lattice members 360 which are described further below. However, it will be understood that any other suitable material suitable for forming an upper microshell layer having the desired characteristics for a given application may alternatively be formed over the first and second sacrificial layers. Examples of such microshell layer characteristics include, but are not limited to, relatively low processing thermal budget, hermicity of formed microshell layer, conductivity of microshell layer for transducer applications or to provide a Faraday cage to isolate underlying devices from electromagnetic interference, transparence to one or more radiation wavelengths such as infrared radiation for underlying sensors, etc. Specific examples of other suitable types of upper microshell materials include, but are not limited to, nitride, titanium aluminide (TiAl), tungsten, etc. Moreover, thickness of upper microshell layer 350 may vary according to the needs of a given application, e.g., formed to be greater than 2 µm or less than 1 µm in other possible embodiments.

Figure 4:
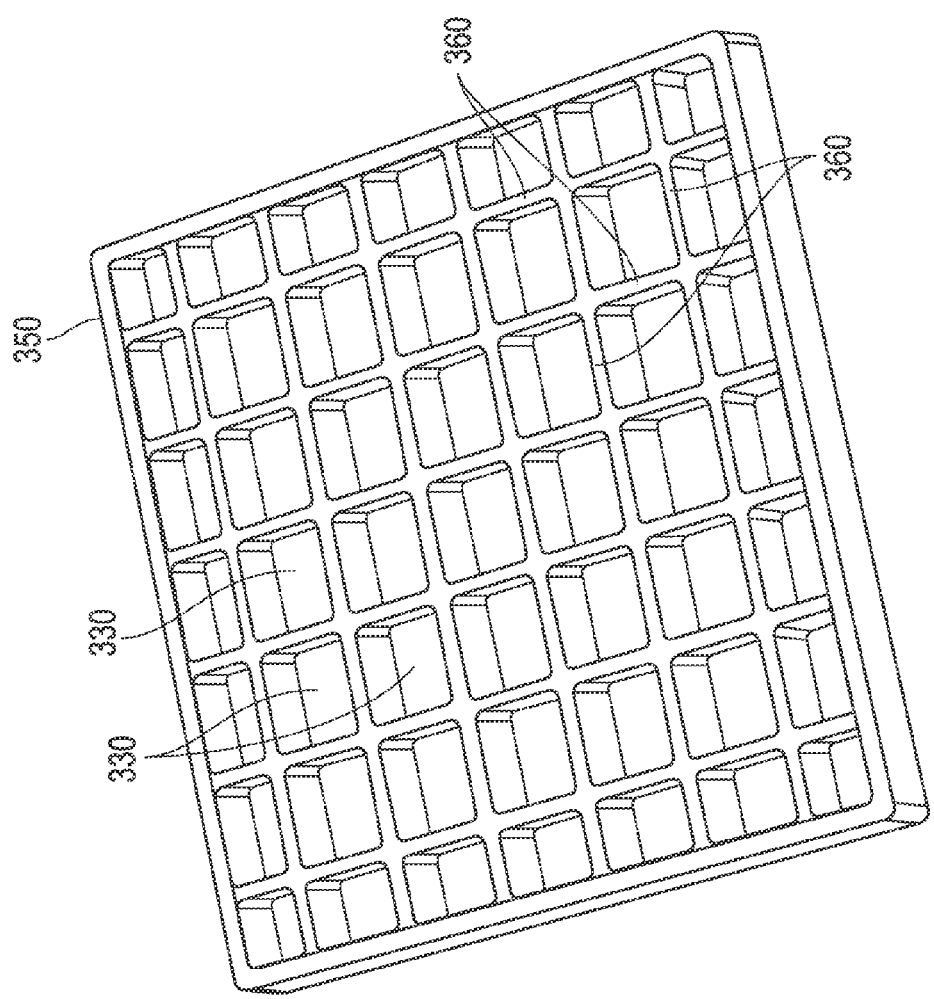
FIG. 4 illustrates a perspective view of the underside of an upper microshell layer structure according to one exemplary embodiment of the disclosed methods and structures.

FIG. 4 illustrates a perspective view of one embodiment of the underside (e.g., interior cavity side) of an upper microshell layer structure 350 as it may be formed to include microshell support lattice members 360 using steps 224 to 228 previously described. In the illustrated embodiment microshell support lattice members 360 have been formed to create an array of square or rectangle cavity sections 330 after removal of the second sacrificial layer from these sections. However, it will be understood that any other configuration of support lattice members may be formed that are suitable for creating other cavity section shapes that are adequate to optimize robustness, stiffness, surface to volume ratio and/or manufacturability. Examples of other such cavity section shapes include, but are not limited to, hexagonal, triangular, disk-shaped, octagonal, etc. As may be seen in FIG. 3, the second sacrificial layer may be patterned to result in a deposited microshell layer 350 having support lattice members 360 that terminate above (and do not contact) MEMS structural layer 315. Rather, the second sacrificial layer may be patterned such that the deposited microshell layer 350 contacts MEMS structural layer 315 at the peripheral edges around cavity sections 330 to suspend the microshell layer 350 and its lattice members 360 over interior cavity sections 330.

In one exemplary embodiment, a second sacrificial layer having a thickness of from about 5 µm to about 20 µm may be deposited at relatively low temperature, and patterned to allow a relatively thin microshell layer 350 to be deposited over the sacrificial layer having a thickness of from about 1 µm to about 2 µm at locations of the layer 350 between the downwardly suspended lattice members 360. Due to the relatively larger thickness of the second sacrificial layer, the second sacrificial layer may be patterned to result in a relatively thicker layer of material 350 at the location of the support lattice members 360 as shown. Thus, in one exemplary embodiment, the microshell layer 350 may be formed with support lattice members 360 having a thickness that is just less than or equal to the overall thickness of the second sacrificial layer before etching (e.g., from less than or equal to about 5 µm to less than or equal to about 20 µm). In one exemplary embodiment, a gap between the base of support lattice members 360 and top of structural layer 315 that is equal to the thickness of the first sacrificial layer, e.g., from about 0.5 µm to about 1 µm. In one embodiment, width (horizontal side-to-side) of individual support lattice members 360 may be less than about twice the thickness of microshell layer 350 as it is measured between the support lattice members 360.

Advantageously, support lattice members 360 may be provided in one exemplary embodiment to strengthen a relatively thin (e.g., about 1 µm to about 2 µm) overlying microshell layer 350 and, in one embodiment, to impart a strength to such an overlying thin microshell layer 350 that is substantially the same as the strength of a relatively thicker microshell layer that has an overall shell thickness that is equivalent to the thickness of the support lattice members 360. In one embodiment, spacing between adjacent individual lattice members 360 may be selected to provide sufficient strength against downward compressional force to meet the needs of given applications, e.g., so at to resist or substantially prevent deflection of microshell layer 350 toward underlying structural layer 315 under anticipated compressional forces for a given application, or so as to limit deflection of microshell layer 350 toward underlying structural layer 315 to a pre-determined amount under anticipated compressional forces of a given application.

Moreover, deposition of a thicker second sacrificial layer may be carried out at relatively lower temperatures than deposition of a thicker microshell layer, and deposition of a thinner microshell layer 350 may be carried out using elevated temperatures for a shorter duration of time than required for deposition of a thicker microshell layer, the latter of which may be incompatible with thermal budget of the process flow and/or more costly. Thus, a relatively thin microshell layer 350 having a relatively lower thermal budget (i.e., shorter microshell deposition time at elevated temperature) may be fabricated with support lattice members 360 to have substantially the same strength as a thicker microshell layer that requires a higher thermal budget (i.e., greater microshell deposition time at elevated temperature). Moreover, in transducer sensor embodiments, a relatively thin overlying upper microshell layer 350 allows for improved sensor sensitivity while the support lattice members 360 allow relatively large volume main cavity sections 330 to be formed under the thin microshell layer structure 350, which provide for greater sensor robustness (e.g., increased vacuum stability against environmental effects) due to increased volume allocated for vacuum space in main cavity sections 330.

Deposited upper microshell layer 350 may then be masked and patterned by etching in step 232 to create release holes 380 as shown in FIG. 3, followed by a two-step release process in step 234. In particular, step 234 may include performance of a first etch step process to remove both first and second sacrificial layers to create first cavity portions 320, open areas 323, and main cavity sections 330 shown in FIG. 3. Step 234 may also include a second etch step (e.g., using hydrogen peroxide) to remove existing sacrificial germanium MEMS release layer in areas 382 of the MEMS region of structure 102, e.g., beneath selected areas of MEMS structural layer 315 to release MEMS devices formed therein. At the end of this second step release etch, an optional hydrogen fluoride etch may be performed to remove any oxide-based protective layer that has been formed over residual gas getter layer 334 to expose interior surfaces of getter layer 334 so that it may contact and scavenge or otherwise remove contaminants from open areas 320, 323 and main cavity sections 330.

Following step 234, the now empty microshell cavity sections 330 may then be vacuum sealed in step 236 with a hermetic sealing layer 390. In one embodiment, sealing layer 390 may be comprised of any material or combination of materials suitable for providing hermicity and that is also compatible with low temperature BEOL IC processing. Examples of suitable materials for forming sealing layer 390 include, but are not limited to, metals such as aluminum, tungsten, copper, titanium, and their alloys. In one exemplary embodiment, sealing layer 390 may be a metal layer that is formed in a vacuum environment using a metal physical vapor deposition tool. Alternative or additional materials that may be employed for sealing layer 390 include non-metals such as SiGe, etc. Moreover, a sealing layer 390 may also comprise multiple metal and/or non-metal layers of different materials. In one embodiment, layer 390 may be an uppermost level of interconnect forming pad structures and/or edge seals, etc. that are typical of an IC (for example metal level nine of a nine level metal BEOL IC process).

In any case, sealing layer 390 (e.g., aluminum or other suitable metal/s) may be formed to seal the release holes 380 in the microshell, trapping the existing process vacuum level in the cavity sections 330, e.g., above MEMS device/s formed in the underlying MEMS structural layer 315. This is illustrated in FIG. 3 where release hole 380 is shown filled with sealing layer 390. In one exemplary embodiment, design and layout may be further selected such that the metal deposition of layer 390 also serves to self-align into pad regions, thus connecting the electrical pads without requiring additional masking step/s as illustrated by pad structure 108, which is illustrated in further detail in relation to FIG. 5.

Figure 5:
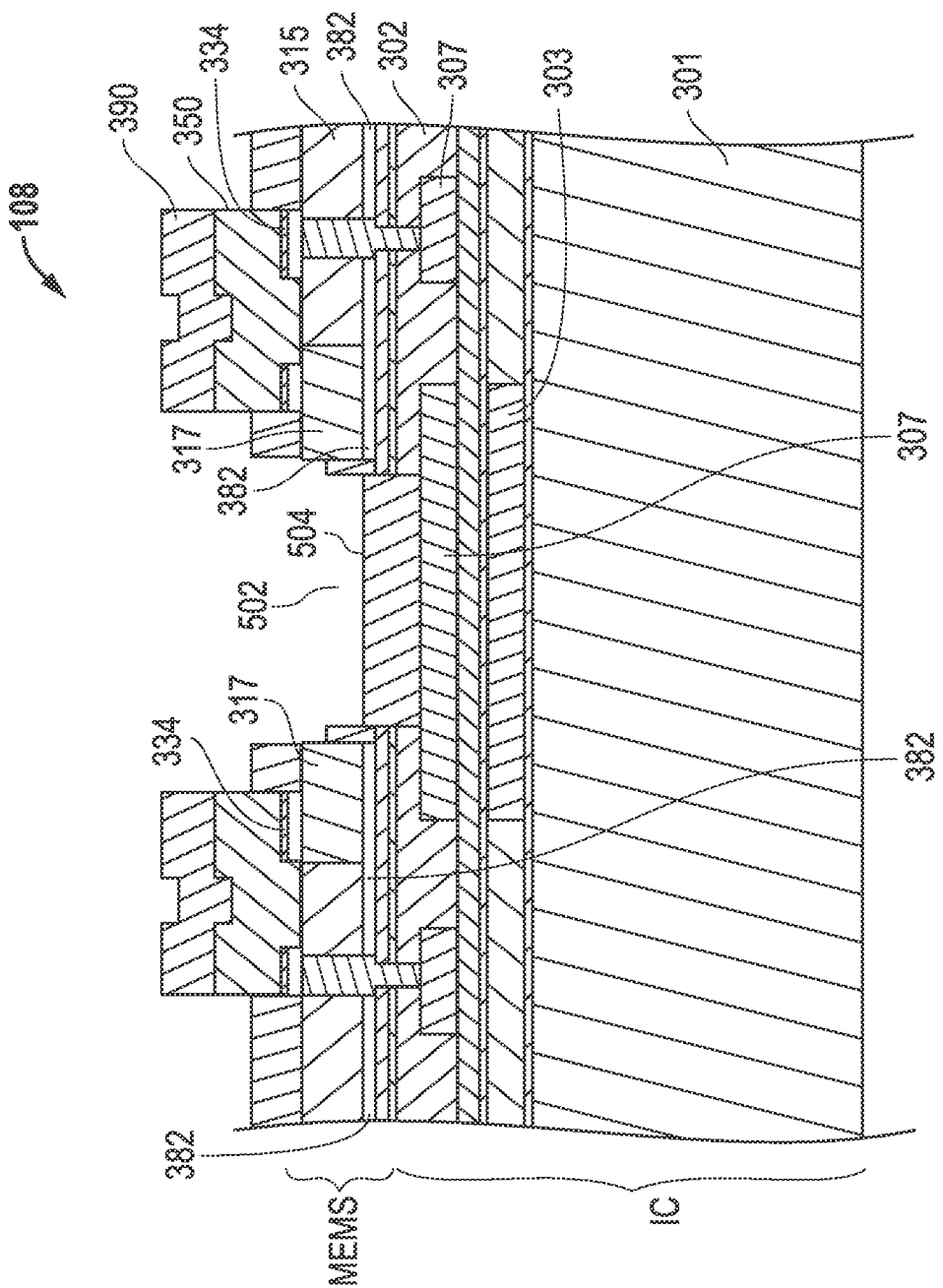
FIG. 5 illustrates a cross-sectional view of a shadow mask pad structure according to one exemplary embodiment of the disclosed methods and structures.

As shown in FIG. 5, pad structure 108 includes a conductive pad 504 that has been formed by shadow mask deposition of conductive sealing layer/s 390 within pad region 502. In this case, the underlying opening of pad region 502 down to metallization layer 307 may be previously formed by MEMS sacrificial and contact patterning step 208, MEMS pad open step 210, and subsequent sacrificial and microshell patterning steps 214, 218 and 232. Thus, self-aligned conductive pad 504 may be then formed by shadow mask deposition of conductive sealing layer 390 after microshell patterning step 232 and release step 234 to connect the electrical pads without the need for additional mask or patterning steps.

When forming vacuum encapsulated device structure 102, process flow 200A may proceed directly to step 244 where wafer level testing may be performed. However, one or more other additional steps may be optionally performed after step 236 to additionally or alternatively form other device structures where desired, such as trapped sacrificial structure 104 (e.g., for relative humidity sensor) and/or membrane transducer structure 106 of FIG. 1.

Figure 6:
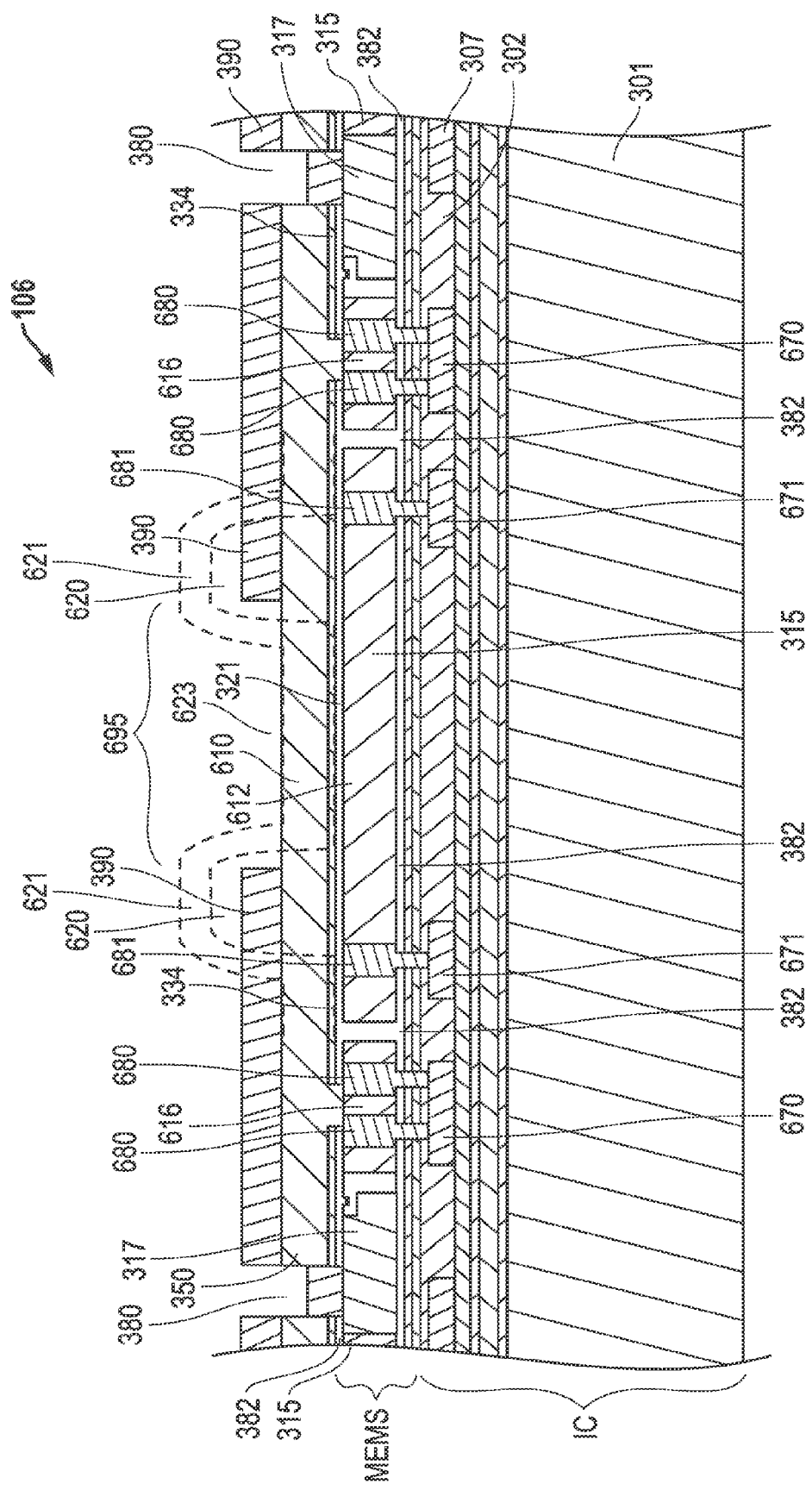
FIG. 6 illustrates a cross-sectional view of a membrane transducer structure according to one exemplary embodiment of the disclosed methods and structures.

For example, FIG. 6 illustrates one exemplary embodiment of a membrane transducer structure 106 that may be formed for a capacitive micromachined ultrasonic transducer "CMUT", in part, by incorporating optional step 238 together with optional step 208 of process flow 200A. As shown in FIG. 6, transducer contacts 616 and optional lower transducer capacitor plate 612 have been patterned from MEMS layer 315 and its underlying sacrificial release layer during optional step 208. During steps 212-214, the first and second sacrificial layers have been patterned such that upper microshell layer 350 forms a transducer membrane 610 that overlies an open area 321 equivalent to the thickness of the first sacrificial layer above lower transducer plate 612. In this regard, the second sacrificial layer may be removed in step 218 so that the upper microshell layer 350 is deposited in step 230 directly over the first sacrificial layer, which is subsequently removed to form open area 321 during two-step release step 234. In one exemplary embodiment, a release hole patterning mask may be used to define compliant support structures at release holes 380 on the sides of the membrane, and/or to use the sealing material in release hole areas 380 as anchors to lower level layer 315.

During optional step 238, the sealing layer 390 may be masked and patterned to form a transducer opening 695 that exposes an upper surface of the transducer membrane 610 to the ambient environment above the membrane transducer structure 106. As shown, the exposed transducer membrane 610 is now suspended between a pair of electrically-coupled transducer contacts 616 patterned from MEMS layer 315 in step 208 to provide electrical interconnection to metallization 307 of a circuitry 670 in the IC region through conductive vias 680. Similar conductive vias 681 may also be provided to electrically couple the lower transducer plate 612 to complementary metallization 307 of a circuitry 671 in the IC region such that relative capacitance between transducer membrane 610 and lower transducer plate 612 may be measured as transducer membrane 610 flexes closer and further away from lower transducer plate 612 due to external stimulus, e.g., such as varying pressure. In another embodiment, a relatively thinner conductive lower transducer plate 612 (e.g., SiGe) may be formed within a relatively thicker area of dielectric material layer 317 that may be left beneath transducer membrane 610, e.g., relatively thin conductive lower transducer plate 612 may be formed on a top surface of dielectric material layer 317 so that it is embedded within, and exposed at, a top surface of a relatively thicker dielectric material layer portion 317 and coupled to circuitry 671 with conductive vias.

In an optional embodiment, selected area/s of second sacrificial layer may be left during steps 212-214 on top of the first sacrificial area in the area of transducer membrane 610 (e.g., only at one or more outer edges of transducer membrane 610). These selected area/s of second sacrificial layer material may be left such that the deposited upper microshell layer 350 (together with optional getter layer 334 where present) forms one or more peripheral out-of-plane decoupling structure/s 621 (e.g., such as upwardly extending hinge structure/s shown in dashed outline in FIG. 6) over the remaining area/s of the second sacrificial layer as an alternative to formation of in-plane portions of transducer membrane 610 in these peripheral area/s. As shown, the out-of-plane decoupling structure/s 621 may be formed around an in-plane central portion 623 of the transducer membrane 210 that is formed by deposited microshell layer 350 over first sacrificial material in those areas where no second sacrificial material is left remaining during steps 212-214. First and second sacrificial materials beneath the transducer membrane 610 may then be subsequently removed during two-step release step 234 to form open areas 620 under out-of-plane decoupling structures 621 (e.g., similar to main cavity sections 330 of FIG. 3 that include combined cavity portions 320 and 324) that are contiguous with open area 321 under central portion 623 of the transducer membrane 610 as shown. Where optional out-of-plane structures 621 are so formed, sealing layer 390 may be optionally masked and patterned to form a transducer opening 695 of sufficient size and dimension to allow optional decoupling structures 621 to extend upward through the transducer opening 695, although in other embodiments sealing layer 390 may be left over at least a portion of decoupling structures 621.

In one embodiment, one or more out-of-plane decoupling structure/s 621 may be optionally formed to help relieve in plane stress for more predictable parametric behavior and increased design flexibility, and further to decouple the membrane 610 from package induced stress so as to increase robustness against temperature variation and offset drift. In one example, four separate out-of-plane structure/s 621 may be formed to be equally spaced around central portion 623 of a circular-shaped, square-shaped or rectangular-shaped membrane transducer 610, e.g., on each of four sides (e.g., in North-South-East-West oriented relationship) around the periphery of the central portion 623, although other shapes of membrane transducers 610 and other numbers and/or arrangement of out-of-plane structures 621 may be employed. In one embodiment, out-of-plane stiffness may remain relatively unchanged to retain sensing properties, while the hinge/s or other decoupling structure/s 621 formed by the conformal deposition on top of the thick second sacrificial layer adds a degree of freedom in the plane to relieve in plane stresses.

Examples of membrane transducer types that may be fabricated in this manner include, but are not limited to, pressure sensors, microphones, capacitive micromachined ultrasonic transducers (CMUTs), light modulators, etc. It will be understood that any suitable capacitance measurement circuitry configuration and methodology known in the art may be implemented within the IC region for measuring the changing capacitance between transducer membrane 610 and lower transducer plate 612, e.g., such as described in U.S. Pat. No. 8,007,167, which is incorporated herein by reference in its entirety.

Figure 7:
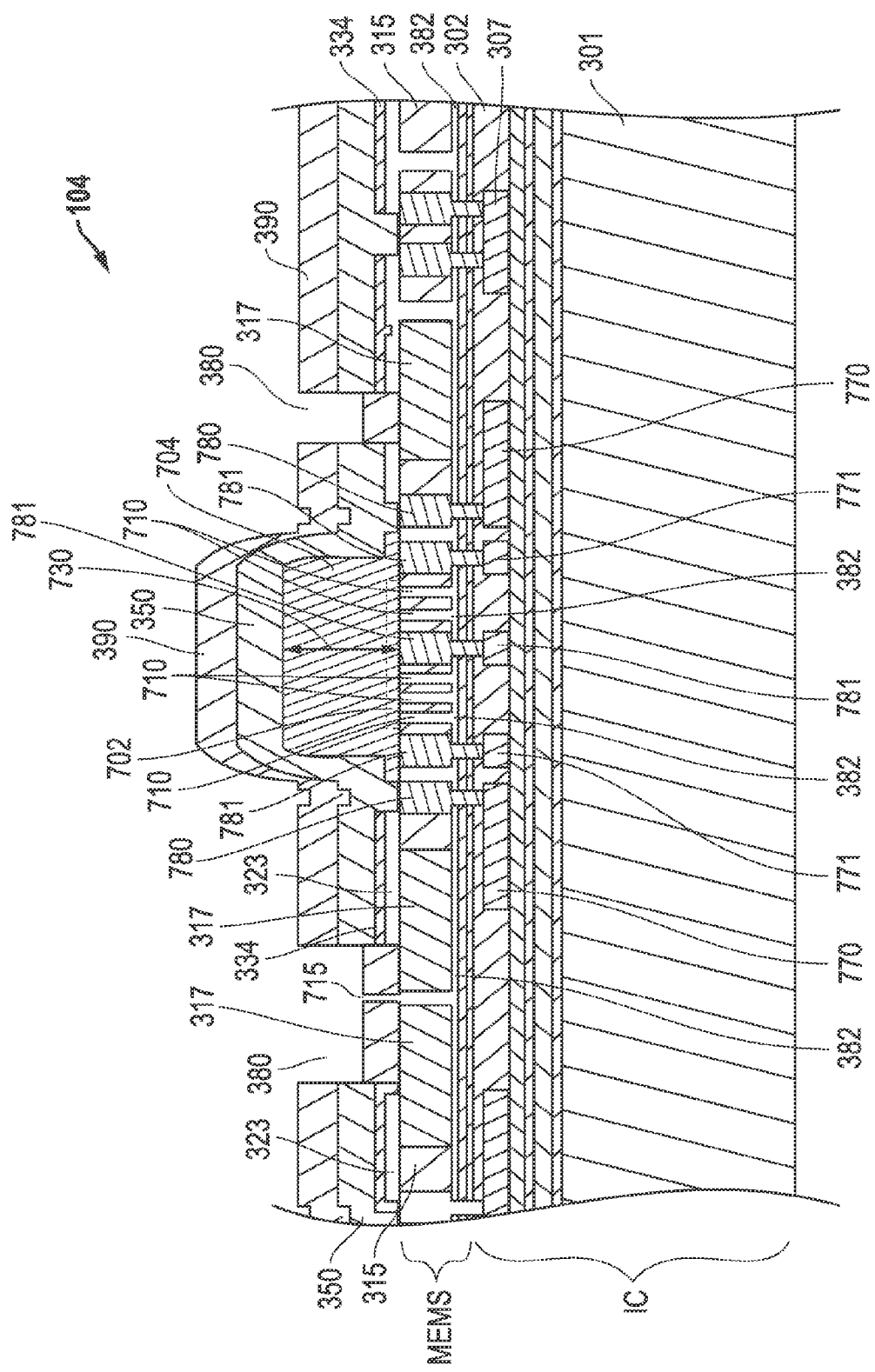
FIG. 7 illustrates a cross-sectional view of a trapped sacrificial structure according to one exemplary embodiment of the disclosed methods and structures.

FIG. 7 illustrates one embodiment of a trapped sacrificial structure 104 (e.g., for a relative humidity sensor) that may be formed, in part, by performing optional step 240 during process flow 200A of FIG. 2A. As shown in FIG. 7, MEMS structural layer 315 has been formed in earlier steps 204-210 to include electrode openings 710 (e.g., formed by patterning of MEMS structural level 315 in step 208) that extend through MEMS layer 315 as shown. As further shown, first sacrificial material 702 and second sacrificial material 704 are each trapped within filled cavity section 730 beneath upper microshell layer 350, and are not removed during two-step release process of step 234 e.g., due to selective presence of intervening structural features and/or selective sacrificial and etchant material selection. In one embodiment, first sacrificial layer 702 may be a polyimide and second sacrificial layer 704 may be polyimide. In one embodiment, first sacrificial layer 702 and/or second sacrificial layer 704 may be a humidity-sensitive polyimide or may be any other humidity sensitive sacrificial material that absorbs water moisture from the surrounding atmosphere and that exhibits different dielectric properties corresponding to the amount of water that the material has absorbed.

As further shown in FIG. 7 a humidity sensor structure may be formed in one exemplary embodiment by removing sacrificial material from beneath MEMS structure layer 315 and from within MEMS electrode openings 710 (e.g., during second germanium etch step of step 234 to also remove sacrificial material remaining in openings 710 after first etch step of step 234) to provide access for ambient atmosphere to contact a capacitor dielectric structure formed by the polyimide or other type humidity-sensitive first sacrificial layer/s 702 and 704. In step 240, second microshell layer 350 and sealing layer 390 may be masked and patterned by etching to create aligned or offset vent hole/s or other inlet openings 715 to provide an access path for ambient atmosphere fluid (e.g., ambient air containing water molecules) to enter the contiguous open area/s 382 beneath MEMS structure layer 315 so that the ambient atmosphere fluid may travel from a given vent hole or inlet opening 715 through a contiguous open area path 382 around conductive vias 780 and 781, and then up through electrode openings 710 to contact the underside of trapped first polyimide layer 702 through electrode openings 710. As shown the inlet openings 715 may be created outside (or laterally offset from) the outer periphery of the capacitor dielectric structure formed by the first sacrificial layer 702 and second sacrificial layer 704. It will be understood that the illustrated embodiment of FIG. 7 having inlet opening defined through dielectric layer 317 (e.g., dielectric material 317 having selective sacrificial and etchant material properties relative to other layers as needed for use in the area of release hole 380 and inlet 715) is exemplary only, and that in other embodiments an inlet opening 715 may be defined in a release hole area 380 through sealing material layer 390 and an underlying structural layer 315, rather than dielectric layer 317 which is not present in the area of release hole 380 in such an alternative embodiment.

In the embodiment of FIG. 7, relative humidity sensor structure 104 may be configured to sense relative humidity by using MEMS structural layer 315 as an electrode for parallel plate capacitance measurement of the alteration of the dielectric properties of the first sacrificial layer polyimide layer 702 due to absorbed water from ambient gas that has penetrated microshell layer 350 through inlet openings 715 and migrated under MEMS structural layer 315 to contact first sacrificial layer 702 through electrode openings 710 as previously described. In one exemplary embodiment, inlet openings 715 and inlet access through a corresponding package hole may be placed away from the effective sensor to allow the decoupling of the sensor size from the package hole size. Since the package hole size determines how small the die and the package can be, a small hole size can help reduce the effective die size without affecting the effective area of the RH sensor. Isolating the sensor from the inlet is also beneficial for robustness and long term stability of the device, e.g., no exposure to mechanical parts during packaging, and no exposure to dust or contaminants during life time of the part.

Advantageously, as illustrated in FIG. 7 the process of FIG. 2A may be adapted (e.g., using optional step 240) to leverage the presence of the sacrificial polyimide in layer 702 as well as the MEMS structural layer 315 as first capacitor plate and upper microshell layer 350 as a second capacitor plate to form a parallel plate capacitive sensor that sandwiches humidity-sensitive polyimide material 702 that has been trapped within filled cavity section 730 during the process sequence. As shown, the second capacitor plate formed from upper microshell layer 350 above the capacitor dielectric structure may be electrically-coupled through conductive vias 780 to metallization 307 of a circuitry 770 in the IC region. Similar conductive vias 781 may also be provided to electrically couple the first capacitor plate formed from MEMS structural layer 315 to complementary metallization 307 of a circuitry 771 such that the changing relative capacitance of the capacitor dielectric structure between the upper and lower capacitor plates may be measured with changing relative humidity of ambient air that enters through inlet opening/s 715.

It will be understood that any suitable capacitance measurement circuitry configuration and methodology known in the art may be implemented within the IC region for measuring the changing relative capacitance of the capacitor dielectric structure between the upper and lower capacitor plates. Just one example of such known techniques and circuitry may be found in U.S. Pat. No. 8,007,167, which is incorporated herein by reference in its entirety. Moreover, it will also be understood that by selection of appropriate capacitor dielectric materials a similar capacitive sensor structural arrangement may be employed to measure any other changing parameter of an ambient atmosphere fluid that enters inlet hole/s 715 and that affects capacitance of a capacitor dielectric structure formed between the upper and lower capacitor plates.

In one embodiment, a stacked parallel plate capacitor-based sensor may be fabricated that offers higher density of capacitance and higher sensitivity to dielectric constant changes than fringing field based sensors. In one exemplary embodiment, a second matched capacitor structure 104 may also be encapsulated in the same process to provide a reference that is not exposed to humidity variation so as to allow a pseudo differential measurement. This may be accomplished, for example, by not forming electrode openings 710 in MEMS structural layer 315 beneath a capacitor dielectric structure of the second matched capacitor structure, i.e., so that the capacitor dielectric structure is fully encapsulated and sealed between the MEMS structural layer 315 and the upper microshell layer 350. The second matched capacitor structure may otherwise be of the same dimensions and configuration as a first capacitor structure having underlying electrode openings 710 in fluid communication with the ambient atmosphere such as illustrated in FIG. 7.

It will be understood that FIG. 2A is exemplary only, and that additional, fewer, and/or alternative steps may be employed as needed or desired to fit a given fabrication application. For example, FIG. 2B illustrates one exemplary embodiment of an alternative process flow 200B that omits steps 224, 226 and 228 so as to form a single structural layer microshell structure that does not include microshell support lattice members 360, and is therefore more flexible. In one exemplary embodiment, a relatively thicker and more flexible microshell structural layer 350 may be deposited in step 230 of process flow 200B than is deposited in corresponding step 230 of process flow 200A in order to compensate for the absence of microshell support lattice members 360, e.g., to achieve a stronger microshell layer over a vacuum cavity without the presence of microshell support lattice members 360.

Figure 8:
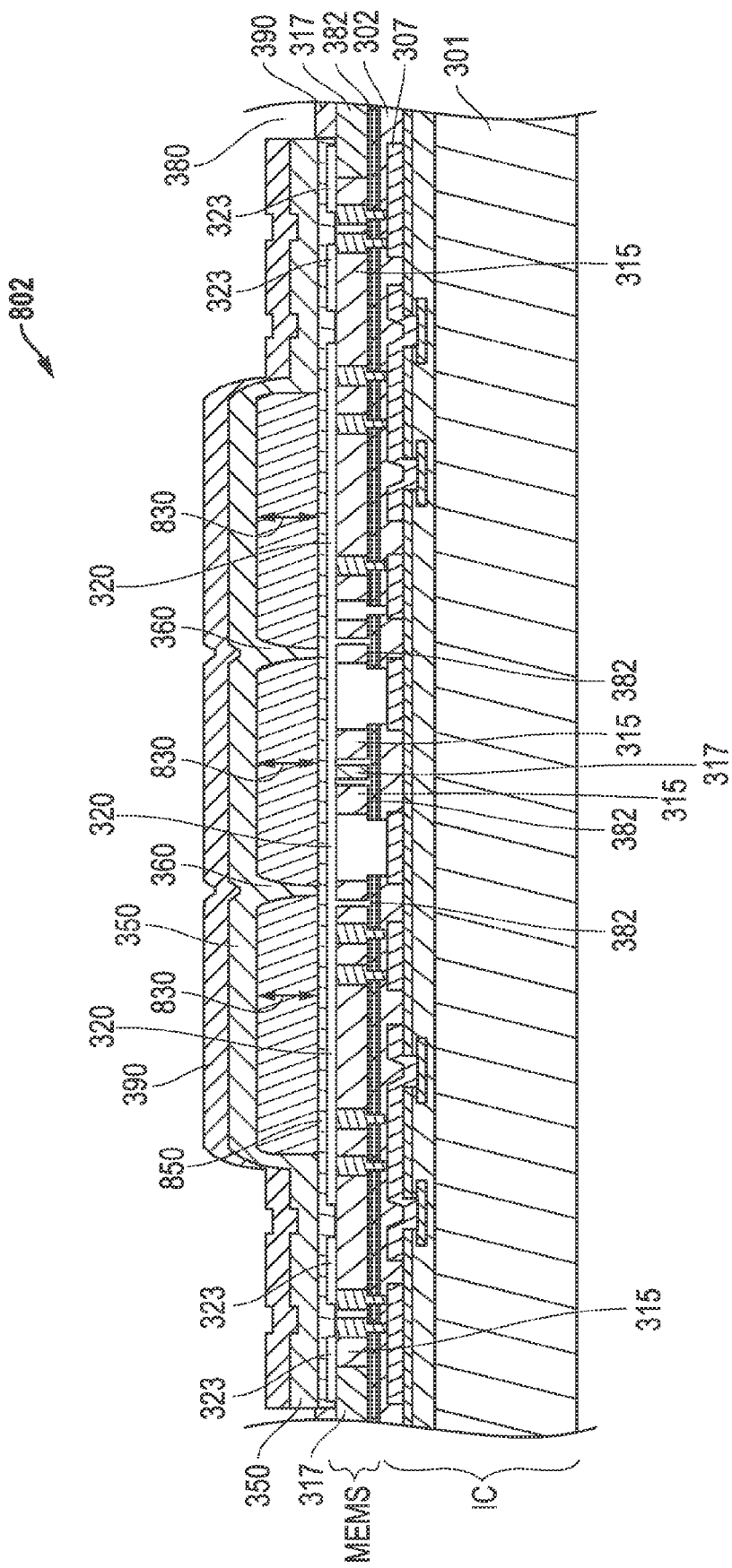
FIG. 8 illustrates a cross-sectional view of a vacuum encapsulated device structure according to one exemplary embodiment of the disclosed methods and structures.

FIG. 2C illustrates one exemplary embodiment of process flow 200C for forming a dual structural layer microshell such as illustrated by the vacuum encapsulated device structure 802 of FIG. 8. As shown, process flow 200C of FIG. 2C includes steps 202-214, which may be performed in a manner similar to the same steps of process flow 200A of FIG. 2A. However, additional steps 290-292 are performed to deposit and pattern a lower microshell layer 850 as shown in FIG. 8 after deposition and patterning of the first sacrificial layer previously described in relation to steps 212-214 of the process flow 200A of FIG. 2A. In particular, a lower microshell layer is deposited in step 290 over the first sacrificial layer to create a lower microshell layer structure 850 as illustrated in FIG. 8.

The lower (or inner) microshell layer may in one embodiment be a silicon germanium (SiGe) material layer that is deposited by a LPCVD or PECVD process to a thickness of from about 0.5 µm to about 2 µm. However, it will be understood that any other suitable material suitable for forming a lower microshell layer 850 having the characteristics to fit a given application (e.g., good selectivity to release and/or sacrificial etchants, electrical conductivity, etc.) may alternatively be formed over the first sacrificial layer. Examples of other suitable types of lower microshell materials include, but are not limited to, nitride, titanium aluminide (TiAl), tungsten, oxide, nitride, TiAl, germanium, multi-layer (metal stack), etc. Moreover, thickness of lower microshell layer 850 may vary according to the needs of a given application, e.g., formed to be greater than 2 µm or less than 0.5 µm in other possible embodiments.

Next, in step 292, the lower microshell layer 850 may be masked and patterned to form offset (i.e., non-overlapping and staggered) release holes 980 in lower microshell structure layer 850 as illustrated in FIGS. 9A-9B. As shown, release holes 980 may be patterned to be offset from release holes 380 that are subsequently formed in upper microshell layer 350 in step 232. In one embodiment, release holes 980 may be offset from release holes 380 with a minimum spacing of about twice the thickness of lower microshell structure layer 850 up to a maximum spacing that is limited by the etch rate of layer 850. In one exemplary embodiment, release holes 980 may be offset from release holes 380 by about 2 µm to about 10 µm, although release holes 980 may be offset from release holes 380 by a distance greater than about 2 µm or a distance of lesser than about 10 µm in other embodiments. In this "fast release" embodiment, upper release holes 380 and lower release holes 980 together form an etchant travel path (e.g., during step 234) through the respective upper microshell layer 350 and lower microshell 850 during release of a MEMS structural device formed in MEMS structure layer 315 beneath lower microshell 850. Downward entry of etchant into upper release holes 380 is illustrated by the arrows in FIG. 9B.

In one exemplary embodiment, the lower release holes 980 may be defined to be laterally closer to a structural device formed in MEMS structure layer 315 beneath microshell layer 850 so as to minimize the lateral etchant travel distance between the lower release holes 980 and the structural device, while at the same time the upper release holes may be defined to be laterally further from the structural device so as to provide the ability to seal the overall structure with sealing material layer 390 (e.g., during sealing layer sputter deposition in step 236) without risk of depositing the sealing material 390 through the lower release holes 980 in critical device areas on or near the released structural device. In this regard, depending on particular sacrificial etch rates and selectivity, a long undercut beneath MEMS structure layer 315 from the periphery of a structural device may not be possible, and therefore the offset lower release holes 980 of this embodiment may be advantageously placed laterally closer to the device to reduce the undercut distance. In one embodiment, filled cavity sections 830 may be ultimately formed as shown in FIG. 8 between upper microshell layer 350 and lower microshell layer 850. In such an embodiment, no release holes contiguous to the cavity sections 830 are patterned in upper and/or lower microshell layers 350/850, such that cavity sections 830 remain filled with second sacrificial material that is not removed in step 234.

In one exemplary embodiment, first sacrificial material 702 may be removed as shown (e.g., in step 234) to form open areas 320 and 323 between lower microshell layer 850 and MEMS structure layer 315. In an alternate embodiment that is similar to the process described in relation to FIG. 7, first sacrificial material 702 may not be removed from beneath lower microshell layer 850, e.g., so as to leave areas 320 and/or 323 filled with trapped first sacrificial material between lower microshell layer 850 and MEMS structure layer 315. As described in relation to FIG. 7, intervening structural features may be formed or otherwise defined to prevent removal of first sacrificial material 702 during etching of step 234 by closing off any existing etchant path from release holes 380 to at least a portion of a first sacrificial material layer 702, e.g., by closing off or not forming release holes 980 of FIG. 9 that would otherwise communicate etchant to this trapped portion of first sacrificial material 702. In such an alternate embodiment, a trapped sacrificial structure of humidity-sensitive first sacrificial layer 702 may be formed beneath lower microshell layer 850 and above MEMS structure layer 315 and may be implemented as a capacitor dielectric structure for a relative humidity sensor in a manner similar to that described in relation to FIG. 7, with the exception that lower microshell layer 850 is configured in this case as a second capacitor plate that together forms a parallel plate capacitive sensor with the first capacitor plate of MEMS structure layer 315 by sandwiching humidity-sensitive polyimide material 702 therebetween. Otherwise similar processing steps as described in relation to FIG. 7 may be employed, i.e., to form electrode openings 710 in MEMS structural layer 315 and open area/s 382 beneath MEMS structure layer 315, together with vent hole/s or other inlet openings 715 to provide an access path for ambient atmosphere to enter the contiguous open area/s 382 beneath MEMS structure layer 315 so that it may travel to contact the underside of trapped first polyimide layer 702 through the electrode openings 710.

Figure 2D:
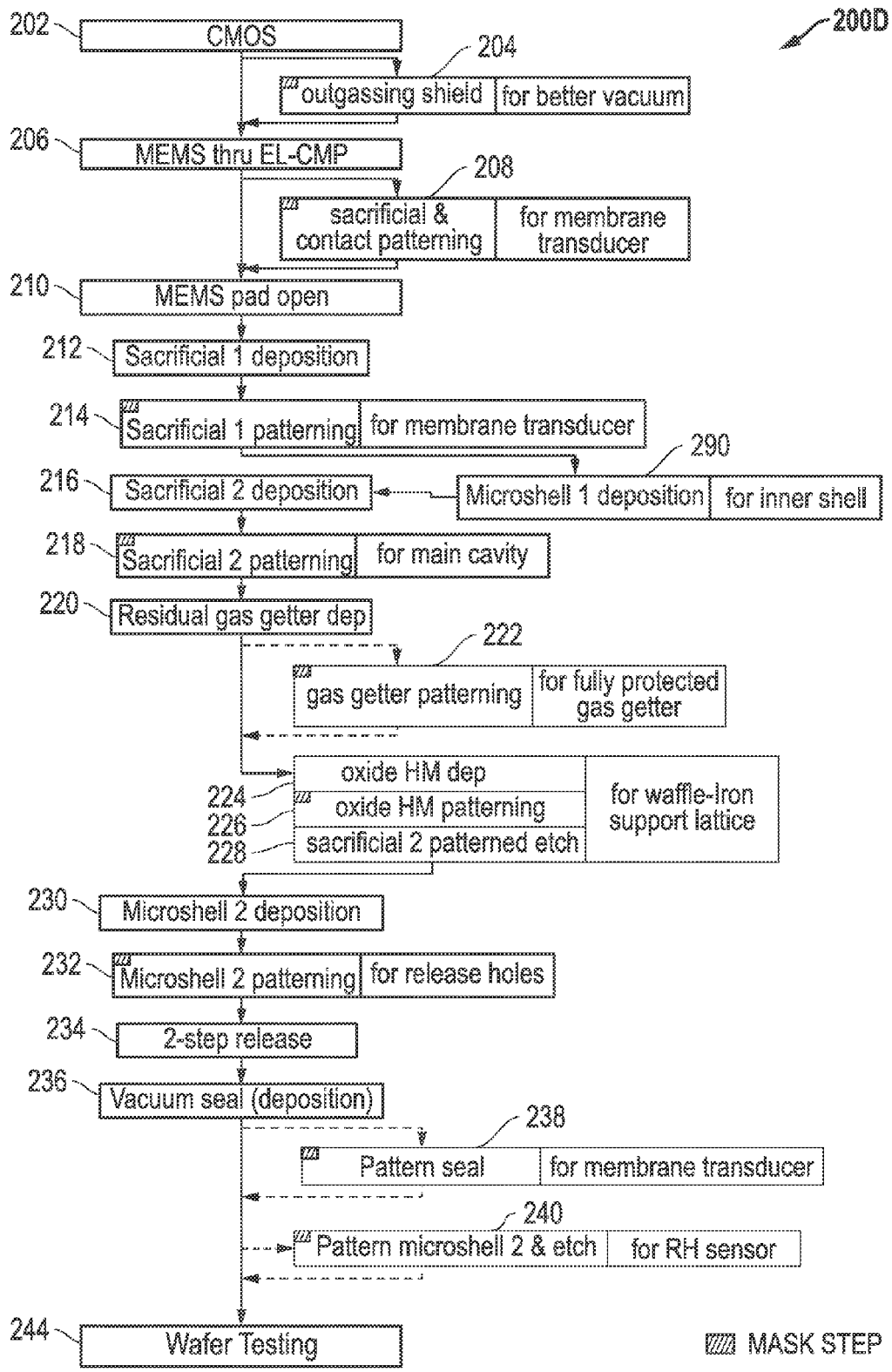
FIG. 2D illustrates a fabrication process flow according to one exemplary embodiment of the disclosed methods and structures.

FIG. 2D illustrates another exemplary embodiment of a process flow 200D for forming a dual structural layer microshell that is similar to the process flow 200C of FIG. 2C, with the exception that step 292 for patterning the offset inner release holes is omitted. In this "edge release" embodiment, release holes are located on the edge/s of the formed structural device rather than at inner locations.

Figure 10:
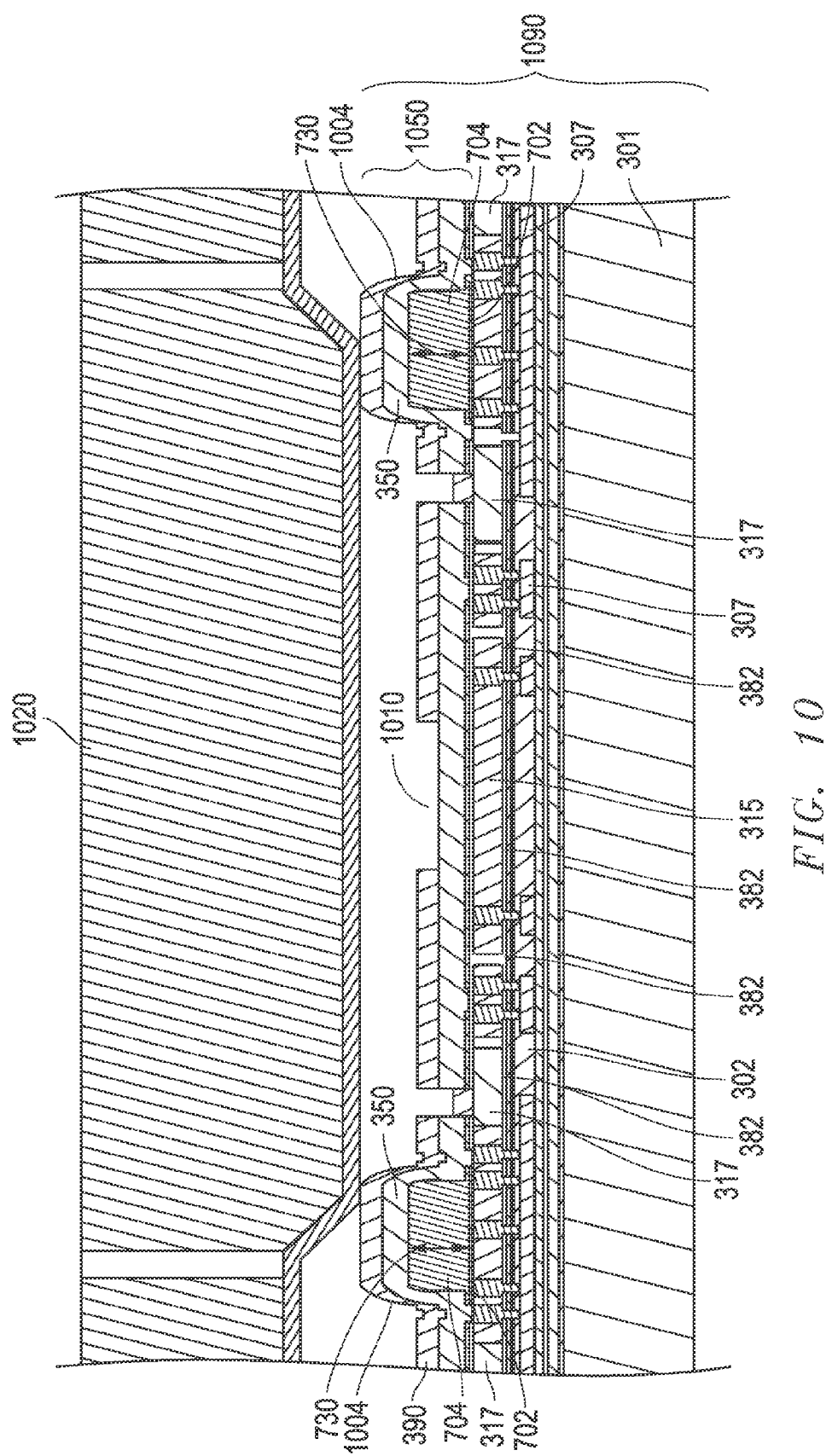
FIG. 10 illustrates a cross-sectional view showing the interaction between a molding tool and a spacer structure according to one exemplary embodiment of the disclosed methods and structures.

FIG. 10 illustrates one embodiment in which two or more trapped sacrificial material structures 1004 may be formed together as a spacer structure 1050 around a relatively fragile or sensitive area 1010 of a semiconductor device die 1090, such as a membrane transducer structure 106 of FIG. 6. As shown in FIG. 10, first sacrificial material 702 and second sacrificial material 704 are each trapped within filled cavity section 730 beneath upper microshell layer 350, and are not removed during two-step release process of step 234 in a manner similar to that described in relation to FIG. 7. Spacer structure 1050 may be useful, for example, in combination with sensors device structures such as environmental sensors (e.g., humidity, pressure, temperature), acoustic sensors, optical sensors and chemical sensors that require an opening in a fabricated package to act as an inlet for light, liquid, vapor, and/or gas toward the underlying sensor device of die 1090. Such a sensor opening is usually achieved using a package molding process that employs high pressure contact with the die using a tool 1020 that pulls a vacuum on the die and can crack the die and/or damage the sensor of the fragile/sensitive area 1010. As shown in FIG. 10, multiple trapped sacrificial material structures 1004 may be spaced apart by an amount suitable for acting as a stand-off to space or separate the molding tool 1020 from the fragile/sensitive area 1010 when the tool 1020 mechanically contacts the die during the molding step, thus improving manufacturability due to improved alignment tolerances.

As used herein, a layer or other structure/feature that is formed over a substrate includes a given layer or other structure/feature that is disposed over and in direct contact with an underlying substrate material (e.g., a semiconductor wafer material) as well as a given layer or other structure/ feature that is not disposed in direct contact with an underlying substrate material but that is instead disposed over one or more intervening layers or other structures/features (e.g., such as intervening cavities, metal layers, and/or insulative layers) that are disposed between the given layer or other structure/feature and the substrate such that the given layer or other structure/feature does not directly contact the underlying substrate. Thus the term "over" connotes both direct overlying contact with an underlying layer or other structure/feature, as well as a non-contacting overlying relationship with an underlying layer or other structure/feature, e.g., with one or more intervening layers or other structures/ features disposed therebetween. Likewise, the term "under" connotes both direct underlying contact with an overlying layer or other structure/feature, as well as a non-contacting underlying relationship with an overlying layer or other structure/feature, e.g., with one or more intervening layers or other structures/features disposed therebetween.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed methods and structures may be utilized in various combinations and/or independently. Thus the invention is not limited to only those combinations shown herein, but rather may include other combinations.

What is claimed is:

1. A trapped sacrificial structure, comprising:
   a MEMS region disposed over a substrate, the MEMS region including a MEMS structural layer;
   a portion of a first sacrificial layer and a portion of a second sacrificial layer disposed over the MEMS structural layer;
   an upper microshell layer disposed over the portions of the first and second sacrificial layers, the first sacrificial layer portion and/or a second sacrificial layer portion being configured to form at least one trapped sacrificial structure under the upper microshell layer; and
   one or more upper release holes defined in the upper microshell layer.

2. The structure of claim 1, where the portion of the first sacrificial layer is disposed partially over and in contact with the MEMS structural layer; where the portion of the second sacrificial layer is disposed over and in contact with the portion of the first sacrificial layer; where the upper microshell layer is disposed over the portions of the first and second sacrificial layers to trap the first and second sacrificial layer portions within a cavity filled with first and second sacrificial material under the upper microshell layer to form the at least one trapped sacrificial structure under the upper microshell layer; and where the trapped sacrificial structure further comprises:
   one or more open cavities or open areas defined under the upper microshell layer and over the MEMS structural layer; and
   a sealing layer that seals the upper release holes in the upper microshell layer.

3. The structure of claim 2, further comprising a semiconductor device die that includes the substrate, the semiconductor device die having multiple individual spacer structures disposed in spaced relationship with each other over the semiconductor device die, each of the spacer structures comprising trapped sacrificial structures; and wherein a top of each of the spacer structures extends to a height above the substrate that is greater than a height of tops of one or more other structures that are disposed over the substrate in an area defined between the multiple spacer structures.

4. The structure of claim 3, where the multiple spacer structures are spaced such that the spacer structures act to prevent a molding tool from contacting the tops of the other structures disposed over the substrate in the area defined between the multiple spacer structures when the molding tool is brought together with the semiconductor device die to contact the tops of the spacer structures.

5. The structure of claim 4, where the other structures disposed over the substrate in the area defined between the multiple spacer structures comprise at least one membrane transducer structure.

6. The structure of claim 2, where the trapped sacrificial structure is configured as a humidity-sensitive capacitor structure; and where the MEMS structural layer is configured as a first sensor electrode, the MEMS structural layer having one or more sensor electrode openings defined to extend through the first sensor electrode of the MEMS structural layer;

where a portion of the second sacrificial layer is disposed over and in contact with the portion of the first sacrificial layer to form a humidity-sensitive capacitor dielectric structure disposed over the sensor electrode openings defined in the MEMS structural layer;

where the upper microshell layer is configured as a second sensor electrode over and in contact with the humidity-sensitive capacitor dielectric structure, the upper microshell layer being configured to trap the first and second sacrificial layer portions within a cavity filled with the first and second sacrificial material of the humidity-sensitive capacitor dielectric structure disposed under the upper microshell layer;

where an open fluid communication path is defined under the MEMS structural layer and through the sensor electrode openings to the underside of the humidity-sensitive capacitor dielectric structure; and where one or more inlet openings are defined in the sealing layer and upper microshell layer that are in fluid communication with the open fluid communication path under the MEMS structural layer and through the sensor electrode openings to the underside of the humidity-sensitive capacitor dielectric structure.

7. The structure of claim 6, where the first sacrificial layer portion trapped within the cavity under the upper microshell layer comprises polyimide.

8. The structure of claim 6, where each of the first and second sacrificial layer portions trapped within the cavity under the upper microshell layer comprises polyimide.

9. The structure of claim 6, where the capacitor dielectric structure has an outer periphery; and where the method further comprises creating the inlet openings in the sealing layer and upper microshell layer outside the outer periphery of the capacitor dielectric structure.

10. The structure of claim 6, further comprising an additional trapped sacrificial structure configured as a non-humidity sensitive matched capacitor structure disposed over the same substrate as the humidity-sensitive capacitor structure; and where a portion of a MEMS structural layer configured as a first sensor electrode having no sensor electrode openings;

where a portion of the second sacrificial layer is disposed over and in contact with the portion of the first sacrificial layer to form a matching capacitor dielectric structure disposed over the portion of the MEMS structural layer having no sensor electrode openings; and where the upper microshell layer is configured as a second sensor electrode over and in contact with the matching capacitor dielectric structure, the upper microshell layer being configured to trap the first and second sacrificial layer portions within a cavity filled with the first and second sacrificial material of the matching capacitor dielectric structure disposed under the upper microshell layer.

11. The structure of claim 1, where the second sacrificial layer is thicker than the first sacrificial layer.

* * * * *